United States Patent [19]

Umezawa et al.

[11] 4,065,616

[45] Dec. 27, 1977

[54] PROCESSES FOR PRODUCTION OF A 1-N-(α-HYDROXY-Φ-AMINO ALKANOYL)-3-DEOXY-5-O-PENTAFURANOSYL NEAMINE AND NEW COMPOUNDS PRODUCED BY THE SAME PROCESSES

[75] Inventors: Hamao Umezawa; Sumio Umezawa, both of Tokyo; Tsutomu Tsuchiya, Yokohama; Isamu Watanabe, Higashimurayama, all of Japan

[73] Assignee: Zaidan Hojin Biseibutsu Kagaku Kenkyu Kai, Tokyo, Japan

[21] Appl. No.: 710,949

[22] Filed: Aug. 2, 1976

[30] Foreign Application Priority Data

Aug. 15, 1975  Japan .................................. 50-98501

[51] Int. Cl.$^2$ ......................................... C07H 15/22
[52] U.S. Cl. .................................... 536/17; 424/180; 536/4; 536/10; 536/18; 536/120
[58] Field of Search ........................ 536/10, 17; 424/18

[56] References Cited

U.S. PATENT DOCUMENTS

| | | | |
|---|---|---|---|
| 3,753,973 | 8/1973 | Umezawa et al. | 536/10 |
| 3,781,268 | 12/1973 | Kawaguchi et al. | 536/10 |
| 3,826,802 | 7/1974 | Kawaguchi et al. | 536/17 |
| 3,886,138 | 5/1975 | Naito et al. | 536/10 |
| 3,897,412 | 7/1975 | Naito et al. | 536/17 |
| 3,904,597 | 9/1975 | Naito et al. | 536/10 |
| 3,923,783 | 12/1975 | Naito et al. | 536/17 |
| 3,925,353 | 12/1975 | Umezawa et al. | 536/10 |
| 3,925,354 | 12/1975 | Umezawa et al. | 536/17 |
| 3,929,761 | 12/1975 | Umezawa et al. | 536/10 |
| 3,929,762 | 12/1975 | Umezawa et al. | 536/17 |
| 3,939,143 | 2/1976 | Umezawa et al. | 536/10 |
| 3,940,382 | 2/1976 | Umezawa et al. | 536/10 |
| 3,948,882 | 4/1976 | Umezawa et al. | 536/17 |
| 3,959,255 | 5/1976 | Chazan et al. | 536/17 |
| 3,960,833 | 6/1976 | Naito et al. | 536/17 |
| 3,981,861 | 9/1976 | Chazan et al. | 536/17 |
| 3,984,393 | 10/1976 | Magerlein | 536/17 |
| 4,003,922 | 1/1977 | Kavadias et al. | 536/17 |

OTHER PUBLICATIONS

Umezawa et al., "Science", vol. 157, pp. 1559–1561, Sept. 1967.

Yagisawa et al., "The Jour. of Antibiotics", vol. XXV, No. 8, 1972, pp. 492–494.

*Primary Examiner*—Johnnie R. Brown
*Attorney, Agent, or Firm*—Herbert W. Taylor, Jr.

[57] ABSTRACT

This invention relates to new processes for the production of a 1-N-(α-hydroxy-ω-aminoalkanoyl)-3'-deoxy-5-O-pentofuranosylneamine, including 3'-deoxybutirosins A and B, as a semi-synthetic antibiotic. This invention further relates to new and useful semi-synthetic antibiotics which are produced by the above new processes.

2 Claims, No Drawings

PROCESSES FOR PRODUCTION OF A 1-N-(α-HYDROXY-Φ-AMINO ALKANOYL)-3-DEOXY-5-O-PENTAFURANOSYL NEAMINE AND NEW COMPOUNDS PRODUCED BY THE SAME PROCESSES

BACKGROUND OF THE INVENTION

1. Field of the Invention

This invention relates to chemical compounds which are antibacterial agents of the type called aminoglycosides and includes chemical processes for their production.

2. Description of the Prior Art

It has been elucidated that drug-resistant bacteria which have been isolated from patients, such as drug-resistant *Staphylococcus aureaus*, drug-resistant *Escherichia coli* and *Pseudomonas aeruginosa* exhibit resistance to Kanamycins by the mechanism that these microorganisms produce phosphotransferase capable of phosphorylating the 3'-hydroxyl group of kanamycins and inactivate these antibiotics. (see the "Science" Vol. 157, page 1559, (1967).

On the basis of this mechanism of resistance of the drug-resistant bacteria, we have considered it possible to produce semi-synthetic antibiotics which are active against kanamycin-resistant bacteria. Thus, we and our colleagues synthesized 3'-deoxykanamycin A (see U.S. Pat. No. 3929761); 3',4'-dideoxykanamycin B (hereinafter abbreviated as DKB) (see Japanese Pat. publication No. 7595/75 and U.S. Pat. No. 3753973); 3'-deoxykanamycin B and 3'-deoxyribostamycin (see U.S. Pat. No. 3929762). It has been found that these deoxy derivatives of aminoglycosidic antibiotics exhibit high antibacterial activity against the above-mentioned resistant bacteria. It has been confirmed that DKB is a very useful and effective semi-synthetic antibiotic in clinical tests.

Furthermore, it has been concluded that a few of drug-resistant gram-negative bacterial (including *Escherichia coli* carrying R-factor) produces a kanamycin-inactivating enzyme capable of nucleotidylating the 2''-hydroxy group of kanamycin and DKB (see the "Journal of Antibiotics" Vol. 25, page 492 (1972) Considering the molecular configuration of kanamycins, we have expected it possible to create such derivatives of aminoglycosidic antibiotics which are not attached by the enzymatic reactions of the kanamycin-inactivating enzymes, if some change occurs in the molecule of kanamycins by modifying the 1-amino group of kanamycins and their analogous aminoglycosdic antibiotics. With this expectation, we and our colleagues have made further research to semi-synthetize various derivatives of aminoglycosidic antibiotics. Thus, 1-N-(4-amino-2-hydroxybutyryl)-DKB; 1-N-(4-amino-2-hydroxybutyryl)-kanamycin; 1-N-isoserylkanamycin; 1-N-isoserylkanamycin B and 1-N-isoseryl-DKB which are active against the kanamycin-resistant bacteria have been synthesized (see British Pat. No. 1426908).

Moreover, we and our colleagues have synthesized such kanamycin B derivatives by acylating both the 1-amino and 2'-amino groups of kanamycin B or DKB with an α-hydroxyamino acid of the formula $H_2N-(CH_2)_n-CH(OH)-COOH$ wherein n is an integer of 1 or 2 (see U.S. Pat. No. 3940382). It has been confirmed that these semi-synthetic kanamycin B derivatives of this type exhibit a high antibacterial activity not only against the kanamycin-sensitive but also kanamycin-resistant bacteria including *Pseudomonas aeruginosa* and which are of a low toxicity.

We have previously proposed some methods of synthetizing a 1-N-(α-substituted-β-aminoalkanoyl)-3'-deoxyribostamycin (see British Pat. No. 2426908 and co-pending Japanese patent application No. 49107/75, co-pendng U.S. Pat. application Ser. No. 676,792 filed on Apr. 14, 1976).

SUMMARY OF THE INVENTION

An object of this invention is to provide a new process for the production of a 1-N-(α-hydroxy-ω-aminoalkanoyl)-3'-deoxy-5-0-pentofuranosylneamine, including the 1-N-(α-hydroxy-ω-aminoalkanoyl)-3'-deoxyribostamycin, which process is different from and more economic and facile to operate than the previously proposed methods mentioned just above. The other object is to provide new and useful semi-synthetic antibiotics which are active against the kanamycin-sensitive bacterial as well as against the kanamycin-resistant bacteria. Another objects will be clear from the following descriptions.

As a result of our research, we have now found that 3'-deoxyparomamine or 3'-deoxyneamine can be converted into its 1,6-carbamate derivative by reacting the N-ethoxycarbonyl or N-benzyloxycarbonyl derivatives of them with sodium hydroxide or sodium hydride in anhydrous organic solvents such as dimethylformamide. We have now further found that the 4'-hydroxyl and 6'-hydroxyl groups and the amino groups of the resulting 3'-deoxyparomamine 1,6-carbamate derivative, as well as the 4'-hydroxyl groups and the amino groups of the resulting 3'-deoxyneamine 1,6-carbamate derivative can readily be protected or blocked by reacting with a known hydroxyl-protecting reagent and a known amino-protecting reagent in such a manner that only the 5-hydroxyl group remains selectively in the free or unblocked state. It has further been found that the protected 3'-deoxyparomamine or 3'-depoxyneamine 1,6-carbamate containing the free 5-hydroxyl group so obtained may readily react with a pentose halide or its functional equivalent (that is, such an active derivative of the pentose containing a reactive group other than the halo group at the 1-position of the pentose moiety) to effect a condensation between the 5-hydroxyl group of the 3'-deoxyparomamine or 3'-deoxyneamine moiety and the 1-function of the pentose, so that the formation of the 5,1''-linkage is involved in the resulting condensation product. Furthermore, it has been found that when the condensation product so derive from the 3'-deoxyparomamine or 3'-deoxyneamine, 1,6-carbamate compound is subjected to hydrolysis under alkaline conditions, the 1,6-carbamate ring is ring-fissioned preferentially to liberate or regenerate the free 1amino group and the free 6-hydroxyl group, without cleaving the amino-protecting groups from the other amino groups of the 1,6-carbamate derivative. The hydrolysis product so obtained containing the free 1-amino group may be reacted with an α-hydroxy-ω-aminoalkanoic acid or its functional derivatives at the carboxylic group thereof, so that the free 1-amino group is efficiently acylated with the α-hydroxy-ω-aminoalkanyol group. Based on these findings, we have devised the new processes according to the present invention.

According to a first aspect of the present invention, therefore, there is provided a process for the production of a 1-N-(α-hydroxy-ω-aminoalkanoyl)-3'-deoxy-5-0-pentofuranosylneamine of the general formula:

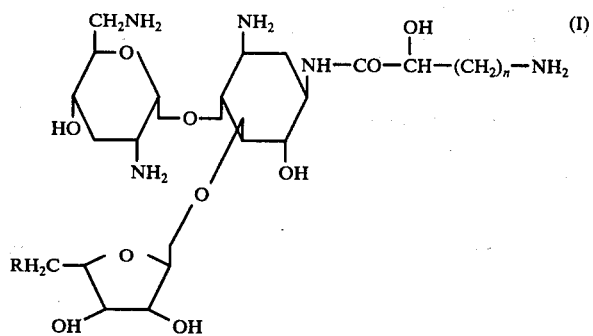

(I)

wherein R is hydroxyl group of amino group, and n is an integer of 1 or 2, which comprises the steps of:

reacting a 3'-deoxyparomamine, 1,6-carbamate derivative of the general formula:

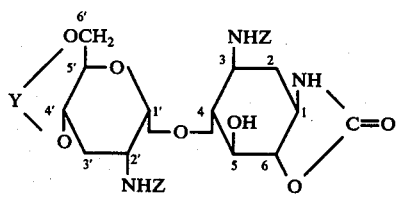

(II)

wherein Y is a di-valent hydroxyl-protecting group selected from an alkylidene or arylidene group of the formula

where $R_1$ and $R_2$ are independently a hydrogen atom, or an alkyl group or an aryl group; or Y is a di-valent hydroxy-protecting group selected from a cycloalkylidene group, tetrahydropyranyl group, carbonyl group and phenylboron group; and Z is an amino-protecting group selected from an alkoxycarbonyl group, an aryloxycarbonyl group, an aralkyloxycarbonyl group, and alkanoyl group, an aroyl group, an alkylsulfonyl group, an arylsulfonyl group and an aralkylsulfonyl group, with a pentofuranosyl compound of the general formula:

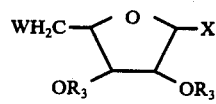

(III)

wherein $R_3$ is a hydroxyl-protecting group selected from an alkanoyl group, an aroyl group, an alkoxycarbonyl group and an aralkoxycarbonyl group; X is a halogen atom, an alkanoyl group or an aroyl group; W is a group of the formula $-OR_3$ where $R_3$ is as defined above, or W is a sulfonyloxy group of the formula $-OSO_2R'$ where $R'$ is an alkyl group, and aryl group or an aralkyl group, or W is a halogen atom or azido group; or with a pentofuranosyl ortho-ester compound of the general formula:

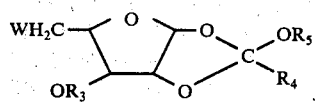

(III')

wherein $R_3$ and W are as defined above, $R_4$ is an alkyl group or an aryl group, and $R_5$ is an alkyl group, to produce a compound of the general formula:

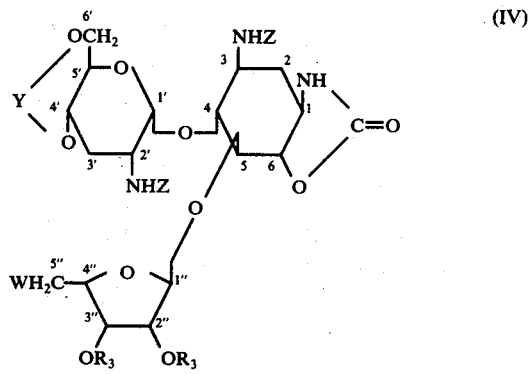

(IV)

or of the formula:

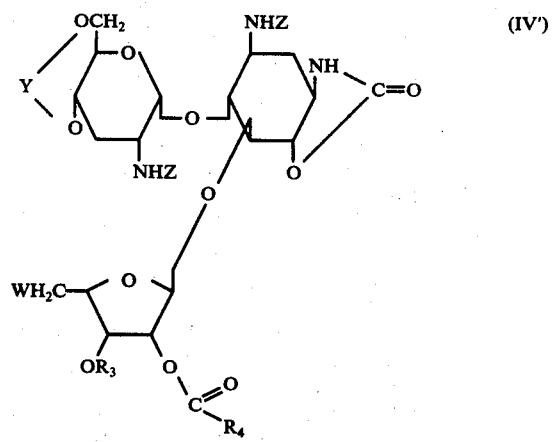

(IV')

wherein $R_3$, $R_4$, Y, A and W are as defined above.

hydrolysing the compound of the formula (IV) or (IV') to remove preferentially the di-valent hydroxyl-protecting group (—Y—) therefrom and to give a compound of the general formula:

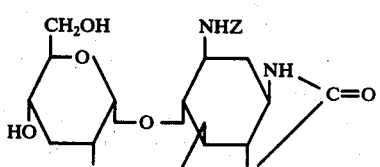

(V)

or of the formula:

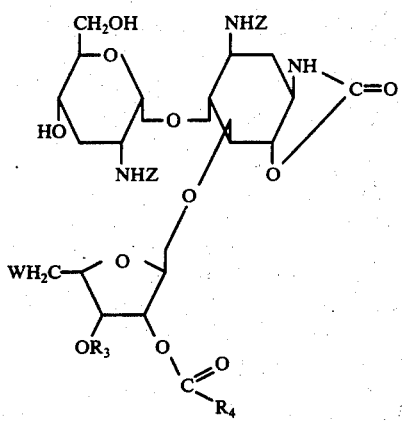
(V')

wherein $R_3$, $R_4$, Z and W are as defined above, reacting the compound of the formula (V) or (V') with a sulfonylating agent of the formula:

$$R_6SO_2T \qquad (VI)$$

wherein $R_6$ is an alkyl group, an aryl group or an aralkyl group, and T is a halogen atom, particularly chlorine or bromine atom, or a group of the formula $-OSO_2R_6$ where $R_6$ has the same meaning as defined above to sulfonylate selectively the 6'-hydroxyl group of the compound of the formula (V) or (V'), reacting the resultant 6'-sulfonylation product with an azidating agent to replace the 6'-sulfonyloxy group by 6'-azido group, occasionally with simultaneous conversion of a 5''-sulfonyloxy group or a 5''-halogeno group into 5''-azido group in case the 5''-sulfonyloxy or 5''-halogeno group is present as the group W in the 6'-sulfonylation product, hydrolysing the resultant 6'-azidation product (including the 6',5''-di-azidation product so occasionally formed) under basic conditions to ring-fission the 1,6-carbamate ring thereof, with formation of the free 1-amino group and free 6-hydroxyl group and with simultaneous removal of a part or all of the remaining hydroxyl-protecting groups, reacting the resultant ring-fission product bearing the free 1-amino group with an α-hydroxy-ω-aminoalkanoic acid of the general formula:

$$HOOC-CH(OH)-(CH_2)_n-NAB \qquad (VII)$$

wherein $n$ is an integer of 1 or 2, and A is hydrogen atom or a known mono-valent amino-protecting group and B is a hydrogen atom or a known mono-valent amino-protecting group, or A and B taken together form a known di-valent amino-protecting group, or with a functional equivalent of said α-hydroxy-ω-aminoalkanoic acid to produce a 1-N-acylation product of the general formula:

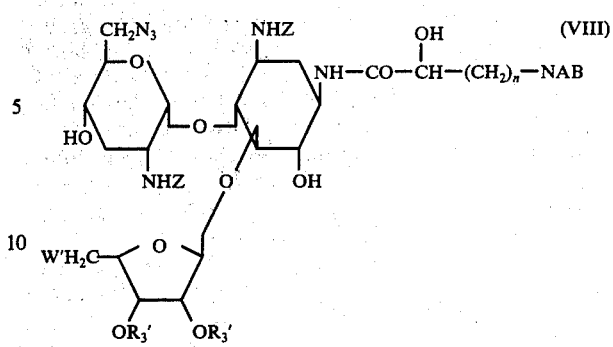
(VIII)

wherein A, B, Z and $n$ are as defined above, $R_3'$ is a hydrogen atom or the group $R_3$ as defined above, and W' is hydroxyl group or azido group, converting by reduction the 6'-azido group and the 5''-azido group, if present, of the 1-N-acylation product (VIII) into amino group(s), and simultaneously or subsequently or both removing the residual protecting groups from the resulting reduction product to produce the desired product of the formula (I).

With respect to the 3'-deoxyparomamine 1,6-carbamate compound which is used as the starting compound in the first aspect process of the present invention, the group Y may be a hydroxyl-protecting group of the formula

where $R_1$ and $R_2$ are independently a hydrogen atom, an alkyl group or an aryl group. When $R_1$ and/or $R_2$ are or is an alkyl group, suitable examples of the alkyl group include an alkyl of 1–4 carbon atoms, for example, methyl, ethyl, propyl, isopropyl, and butyl. When $R_1$ and/or $R_2$ are or is an aryl group, suitable examples of the aryl group include phenyl, methylphenyl and methoxyphenyl. When Y denotes a cycloalkylidene group, suitable examples thereof include a cycloalkylidene group of 5–7 carbon atoms, for example, cyclopentylidene, cyclohexylidene and cycloheptylidene. Y may also be tetrahydropyranyl group

carbonyl group or phenylboron group. When the amino-protecting group Z is an alkoxycarbonyl group, particularly an alkoxycarbonyl of 1–4 carbon atoms, suitable examples thereof include methoxycarbonyl, ethoxycarbonyl, propoxycarbonyl, isopropoxycarbonyl, butoxycarbonyl and t-butoxycarbonyl. When Z is an aryloxycarbonyl group, suitable examples thereof include phenoxycarbonyl and p-nitrophenoxycarbonyl. When Z is an aralkoxycarbonyl group, suitable examples thereof include benzyloxycarbonyl, p-methoxybenzyloxycarbonyl, p-ethoxybenzyloxycarbonyl, p-chlorobenzyloxycarbonyl and p-nitrobenzyloxycarbonyl. When the amino-protecting group Z is an alkanoyl group, it may be the residue of an aliphatic carboxylic acid of 2–5 carbon atoms, for example, acetyl, propionyl, butyryl and valeryl. When Z is an aroyl group, suitable examples thereof may be benzoyl, p-nitrobenzoyl and naphthoyl. When Z is an alkylsulfonyl group, an example thereof may be an alkylsulfonyl group of 1-4 carbon atoms, for example, methylsulfonyl, ethylsulfonyl, propylsulfonyl and butylsulfonyl. When Z is an arylsulfonyl group, an example thereof may be p-toluenesulfonyl, o-nitrobenzenesulfonyl, p-nitrobenzenesulfonyl and 2-naphthalenesulfonyl. An aralkylsulfonyl group for the group Z may be benzylsulfonyl, for example.

As an example of the pentofuranosyl compound of the general formula (III) or (III'), there may generally be mentioned a pentofuranosyl compound, including the $\beta$-D-ribofuranosyl derivative, $\beta$-D-xylofuranosyl derivative, $\alpha$-L-arabinofuranosyl derivative and 5-amino-5-deoxy-$\beta$-D-xylofuranoxyl derivative.

With respect to the pentofuranosyl compound of the formula (III) or (III'), the hydroxyl-protecting group $R_3$ may be an alkanoyl group. Suitable examples of the alkanoyl group include an alkanoyl of 2-5 carbon atoms, for example, acetyl, propionyl and butyryl. When $R_3$ is an aroyl group, suitable examples thereof include benzoyl, p-chlorobenzoyl and p-nitrobenzoyl. When $R_3$ is an alkoxycarbonyl group, suitable examples thereof include an alkoxycarbonyl group of 2-6 carbon atoms, for example, ethoxycarbonyl, t-butoxycarbonyl and amyloxycarbonyl. When $R_3$ is an aralkoxycarbonyl group, it may be, for example, benzyloxycarbonyl, p-methoxybenzyloxycarbonyl, p-ethoxybenzyloxycarbonyl, p-chlorobenzyloxycarbonyl and the like. The group W may be an alkylsulfonyloxy group such as one of 1-4 carbon atoms, for example, methylsulfonyloxy and ethylsulfonyloxy; an arylsulfonyloxy group such as toluenesulfonyloxy; and an aralkylsulfonyloxy group such as benzylsulfonyloxy. The group W may be a protected hydroxyl group —$OR_3$ but it may also be a halo group such as chloro, bromo and iodo, or azido group which is readily convertible into amino group.

The group X may particularly be a halogeno substituent which is selected from bromine, iodine, chlorine and fluorine. With respect to the pentofuranosyl ortho-ester compound of the formula (III'), the group $R_4$ may be an alkyl group, particularly an alkyl of 1-4 carbon atoms, for example, methyl, or an aryl group such as phenyl and p-nitrophenyl. The group $R_5$ may be an alkyl group, particularly an alkyl of 1-4 carbon atoms, such as methyl, ethyl, propyl, n-butyl and t-butyl. The pentofuranosyl ortho-ester compound (III') is in the form of the 1,2-cis-ortho-ester. The pentofuranosyl 1-halogenide (III) may be conventionally prepared from a corresponding O-protected free sugar or 1-0-acyl sugar by the action of halogenating agent such as thionyl chloride or hydrobromic acid in acetic acid. Also, the pentofuranosyl ortho-esters (III') may be conventionally prepared, for example, from 0-acyl-1-halogenide by the action of an alkanol and a base.

In the first aspect process of the present invention, the step of reacting the 3'-deoxyparomamine 1,6-carbamate compound (II) with the pentofuranosyl compound (III) or (III') is carried out in a reaction medium consisting of a solvent which is inert to the condensation reaction and in which the reagents employed are at least partially soluble. The available solvent for this purpose may be dichloromethane, chloroform, tetrahydrofuran, dioxane, dimethylformamide, dimethylacetamide, acetonitrile, nitromethane, benzene, toluene and ethylether, etc. The condensation reaction may suitably take place in the presence of mercuric cyanide, mercuric bromide, silver carbonate, silver oxide, or pyridine, etc., in order to promote the condensation. The reaction may be carried out at a temperature of from 0° C to 150° C for a time of 0.5 to 48 hours.

The step of hydrolysing the compound (IV) or (IV') so formed in the above condensation step is carried out either under acidic conditions, for example, using dilute hydrochloric acid, or an aqueous aliphatic carboxylic acid such as aqueous acetic acid and aqueous phosphoric acid, or under basic conditions, for example, using a limited amount of aqueous barium hydroxide. Through this hydrolysis, the group Y as a part of the hydroxyl-protecting groups is removed or cleaved preferentially to produce the compound (V) or (V').

In the subsequent step, the compound (V) or (V') is reacted with the sulfonylating agent (VI) of the formula $R_6SO_2T$, so that the 6'-hydroxyl group is preferentially sulfonylated, giving the 6'-sulfonylation product. With respect to the sulfonylating agent (VI), the group $R_6SO_2$— may be an alkylsulfonyl group, particularly containing 1-4 carbon atoms, for example, methylsulfonyl, ethylsulfonyl, propylsulfonyl and butylsulfonyl. The group $R_6$-$SO_2$— may also be an arylsulfonyl group, for example, p-toluenesulfonyl, o-nitrobenzenesulfonyl, p-nitrobenzenesulfonyl and 2-naphthalenesulfonyl. The group $R_6SO_2$— may be an aralkylsulfonyl group, for example, benzylsulfonyl. The group T is a halogeno group, particularly chlorine or bromine radical. The group T may be a group —$OSO_2R_6$ where $R_6$ is an alkyl group, an aryl group or an aralkyl group, so that the sulfonylating agent (VI) is a sulfonic anhydride. Suitable examples of the sulfonic anhydride may be methylsulfonic anhydride and toluenesulfonic anhydride. The sulfonylation reaction may be better carried out in a reaction medium in which the reagents are soluble. Any organic solvent which is inert to the sulfonylation may be used as the reaction medium and may be, for example, pyridine, dioxane and methylene chloride. Generally, the sulfonylation reaction may be effected at a temperature in the range of —10° to 150° C.

In the next step, the 6'-sulfonylation product so formed in the above step is reacted with an azidating agent to replace the 6'-sulfonyloxy group by 6'-azido group, so that the 6'-azidation product is produced. Suitable examples of the azidating agent available for this purpose include an alkali metal azide such as sodium azide and potassium azide, as well as ammonium azide. This azidation reaction may be effected in an organic solvent such as dimethylformamide, acetonitrile, dioxane, pyridine, dichloromethane and the like. In case the aforesaid 6'-sulfonylation product to be azidated further contains a 5"-sulfonyloxy or 5"-halogeno group as the group W, the 5"-sulfonyloxy or 5"-halogeno group is also converted into the 5"-azido group during this azidation step, giving the 6',5"-di-azidation product.

The resulting 6'-azidation product or the 6',5"-di-azidation product is then hydrolyzed in a further next step under basic conditions using, for example, a basic reagent such as sodium hydroxide, barium hydroxide and sodium carbonate, so that the 1,6-carbamate ring of the 6'-azidation product (including the 6',5"-diazidation product) is opened with formation or liberation of the free 1-amino group and the free 6-hydroxyl group. During this hydrolysis step, the hydroxyl-protecting groups $R_3$ present at the 2",3"- and 5"-positions may also be removed occasionally by hydrolysis.

The ring-fission product bearing the 1-amino group so formed is then interacted with an ω-hydroxy-ω-aminoalkanoic acid of the general formula:

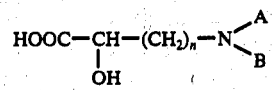

(VII)

wherein $n$ is an integer of 1 or 2, and A is a hydrogen atom or a known mono-valent amino-protecting group and B is a hydrogen atom or a known mono-valent aminoprotecting group, or A and B taken together form a known di-valent amino-protecting group, or with a functional equivalent of said α-hydroxy-ω-aminoalkanoic acid to produce a 1-N-acylation product of the aforesaid general formula (VIII) or (VIII'). As a functional equivalent of the α-hydroxy-ω-aminoalkanoic acid (VII), there may be mentioned a reactive derivative at the carboxyl radical of the α-hydroxy-ω-aminoacid, for example, an acid halide, an acid anhydride, a mixed acid anhydride, an acid azide or an active ester such as the N-hydroxysuccinimide ester thereof. With the amino acid compound (VII) which is employed as the acylation agent, the groups A and B may each be a hydrogen atom. When either of A and B is a monovalent amino-protecting group, it may preferably be an acyl group such as an alkanoyl group and an aroyl group, or an alkoxycarbonyl group, an aralkoxycarbonyl group or an aryloxycarbonyl group, or a sulfonyl group. When the groups A and B taken together form a known di-valent amino-protecting group, it may preferably be an alkylidene group or an arylidene group. Suitable examples of the mono-valent amino-protecting groups A and B include an alkanoyl group of 2–5 carbon atoms such as acetyl; an aroyl group such as benzoyl and o-nitrobenzoyl; an alkoxycarbonyl group of 2–5 carbon atoms such as t-butoxycarbonyl and t-amyloxycarbonyl; an aralkoxycarbonyl group such as benzyloxycarbonyl, p-nitrobenzyloxycarbonyl and p-methoxybenzyloxycarbonyl; an aryloxycarbonyl group such as phenoxycarbonyl and p-methoxyphenoxycarbonyl; a alkylsulfonyl group of 1–4 carbon atoms such as methylsulfonyl and ethylsulfonyl; an arylsulfonyl group such as p-nitrobenzenesulfonyl; and an aralkylsulfonyl group such as benzylsulfonyl and the like.

When the groups A and B taken together form a di-valent amino-protecting group, it may preferably be a group of the formula

or of the formula ΔCHD where D is an alkyl group or an aryl group. Suitable example of the di-valent aminoprotecting group of the type

is phthaloyl. Suitable example of the di-valent aminoprotecting group of the alkylidene or arylidene type =CHD is such one where D is an alkyl group such as methyl, ethyl, propyl and butyl; or an aryl group such as phenyl, p-methoxyphenyl, p-chlorophenyl and p-nitrophenyl.

In this 1-N-acylation step, the reaction is better carried out in a reaction medium comprising a solvent in which the reagents employed are soluble and which is inert to the acylation reaction. As the solvent for this purpose, there may be employed water, tetrahydrofuran, dioxane, ethyleneglycol, dimethylether, dimethylformamide, dimethylacetamide and propyleneglycol dimethylether, or a mixture of two or more of them. In particular, a mixed solvent composed of water and tetrahydrofuran is preferred. The 1-N-acylation reaction may most suitably be carried out at a temperature of up to 50° C and desirably at a temperature of up to 25° C.

The α-hydroxy-ω-aminoalkanoic acid (VII) which is used as the acylating agent in the present invention may either be in the racemic form or in an optically active form, although it is preferred to use a compound of L-form on account of antibacterial activity of the final product, for example, when α-hydroxy-γ-aminobutyric acid (n=2) is employed as the 1-N-acylation agent.

The 1-N-acylation product (VIII) is then reduced. In this reduction step, the 6'-azido group of the 1-N-acylation product (VIII) is converted into the 6'-amino group. If the 5"-azido group is present in the 1-N-acylation product (VIII), this 5"-azido group is simultaneously converted into the 5"-amino group, too. The reduction of the 1-N-acylation product (VIII) is carried out either by treating with hydrogen in the presence of a hydrogenation catalyst such as palladium, platinum, Raney nickel, rhodium, ruthenium and nickel, or by treating with an alkali metal such as lithium metal and sodium metal in liquid ammonia at a low temperature, whereby the 6'-azido group of the 1-N-acylation product (VIII) is converted into the 6'-amino group, occasionally with simultaneous conversion of the 5'-azido group into the 5"-amino group if the 5"-azido group is present initially in the 1-N-acylation product. When this reduction step is effected by reduction with hydrogen, the amino-protecting groups Z at the 3- and 2'-positions as well as the amino-protecting groups A and B can be removed concurrently by hydrogenolysis depending on whether the nature of the groups Z, A and B (such as an aralkoxycarbonyl group) is such one which is cleavable by hydrolgenolysis. When the reduction step is effected by the catalytic reduction with hydrogen as mentioned above, the reaction medium in which the reduction takes place may comprise a mixture of water and a water-miscible organic solent such as dioxane, tetrahydrofuran, ethyleneglycol dimethylether, propyleneglycol dimethylether and the like. The catalytic reduction with hydrogen may suitably be carried out at a reaction temperature of 0°–100° C for a reaction duration of 0.5–48 hours using a hydrogen gas at a pressure of 1–5 atms.

The above-mentioned reduction step gives the 6'-amination product or the 6',5"-diamination product, occasionally with simultaneous removal therefrom of a part or all of such hydroxyl-protecting groups and such amino-protecting groups which are existing in the aforesaid 1-N-acylation product (VIII) and which are cleavable by hydrogenolysis. If the resulting 6'-amination product or 6',5"-diamination product still contains the residual protecting groups, the residual protecting groups are necessary to be removed in the final step. The residual protecting groups may be parts or all of the amino-protecting groups A, B and Z. For instance, when the residual amino-protecting groups are an acyl group, an alkoxycarbonyl group or trityl group, these may be removed in a conventional manner by hydrolysis using a base or an acid. When an aralkyloxycarbonyl group or benzoyl group remains as the residual amino-protecting group, it may be removed by reduction with hydrogen in the presence of a catalyst selected from palladium, platinum, Raney nickel, rhodium, ruthenium and nickel. The reduction for this purpose may similarly be carried out in a known manner and under such reaction conditions which are stated for the aforesaid reduction step of producing the 6'-amination product. A preferred catalyst for this purpose is palladium-on-carbon. When an alkylsulfonyl group, an aralkylsulfonyl group or an arylsulfonyl group remains as the residual amino-protecting group, it may be removed in a known manner, for example, by photolysis, by decomposition with radical or by reductive decomposition with an alkali metal such as sodium metal or lithium metal in liquid ammonia. The removal of these sulfonyl groups may conveniently be effected by treatment with sodium metal in liquid ammonia. If a part or all of the hydroxyl-protecting groups are remaining as the residual protective group, it may be removed in a known manner depending on the nature of the residual hydroxyl-protecting group. For instance, the residual hydroxyl-protecting group is of the acyl type, it may be removed by alkaline hydrolysis using aqueous sodium hydroxide, ammonia in methanol or sodium methylate in methanol. In general, the removal of the residual protecting groups is accomplishable in a conventional manner which is known to the skilled in the art depending and suitable for the nature of the protective groups employed.

In this way, the final product of the formula (I) is produced, and it may be purified in a known manner by a chromatographic purification method using CM-Sephadex C-25 (a product of Pharmacia Co., Sweden; a weak cation-exchanger comprising a three-dimentional network gel of dextran bearing carboxymethyl radicals as the cation-exchanger functions), for example. Thus, a pure product of the 1-N-(α-hydroxy-ω-aminoalkanoyl)-3'-deoxy-5-0-pentofuranosylneamine of the formula (I) is obtained.

When the process according to the first aspect of the present invention is followed, the desired 1-N-(α-hydroxy-ω-aminoalkanoyl)-3'-deoxy-5-0- pentofuranosylneamine of the formula (I) is synthetized starting from the protected 3'-deoxyparomamine 1,6-carbamate derivative of the formula (II) through the series of reaction steps as stated hereinbefore. While, we have found it possible also to synthetize the desired compound of the formula (I) starting from a protected 3'-deoxyneamine 1,6-carbamate derivative through a similar series of reaction steps as stated hereinafter.

According to a second aspect of the present invention, therefore, there is provided a process for the production of a 1-N-(α-hydroxy-ω-aminoalkanoyl)-3'-deoxy-5-O-pentofuranosylneamine of the above general formula (I), which comprises the steps of:

reacting a 3'-deoxyneamine 1,6-carbamate derivative of the general formula:

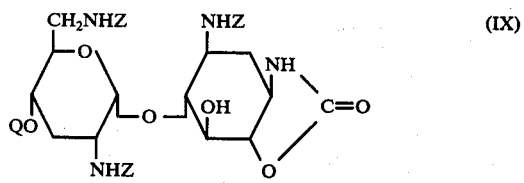

wherein Q is a mono-valent hydroxyl-protecting group selected from an alkanoyl group, an aroyl group, an alkoxycarbonyl group, an aryloxycarbonyl group and an aralkoxycarbonyl group, and Z is an amino-protecting group selected from an alkoxycarbonyl group, an aryloxycarbonyl group, an aralkoxycarbonyl group, an alkanoyl group, an aroyl group, an alkylsulfonyl group, an arylsulfonyl group and an aralkylsulfonyl group, with a pentofuranosyl compound of the general formula:

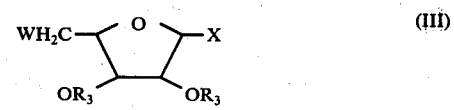

wherein R$_3$, X and W are as defined hereinbefore, or with a pentofuranosyl ortho-ester compound of the general formula:

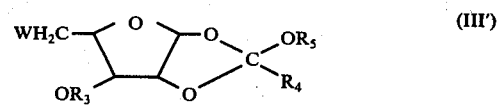

wherein R$_3$, R$_4$, R$_5$ and W are as defined hereinbefore, to produce a compound of the general formula:

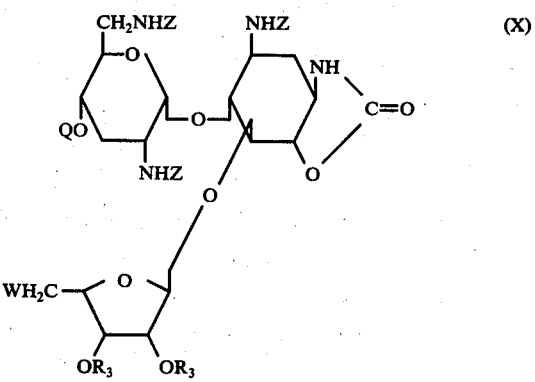

or of the formula:

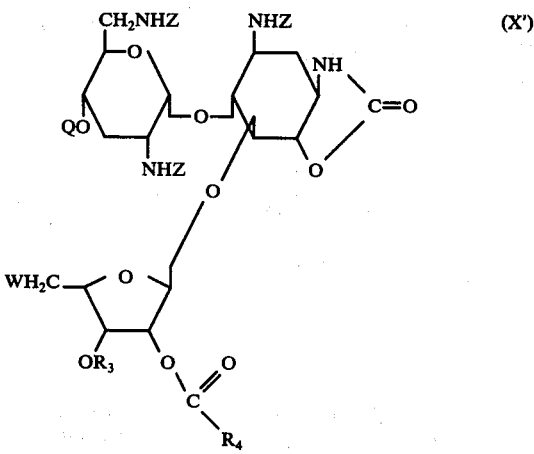

wherein R$_3$, R$_4$, Q, Z and W are as defined hereinbefore, hydrolysing the compound of the formula (X) or (X') under basic conditions to ring-fission the 1,6-carbamate ring with liberation of the free 1-amino group and free 6-hydroxyl group and with simultaneous removal of a part or all of the hydroxyl-protecting groups, reacting the resultant ring-fission product bearing the free 1-amino group with an α-hydroxy-ω-aminoalkanoic acid of the general formula:

$$HOOC-CH(OH)-(CH_2)_nNAB \quad (VII)$$

wherein n, A and B are as defined hereinbefore, or a functional equivalent of said α-hydroxy-ω-aminoalkanoic acid to produce a 1-N-acylation product of the general formula:

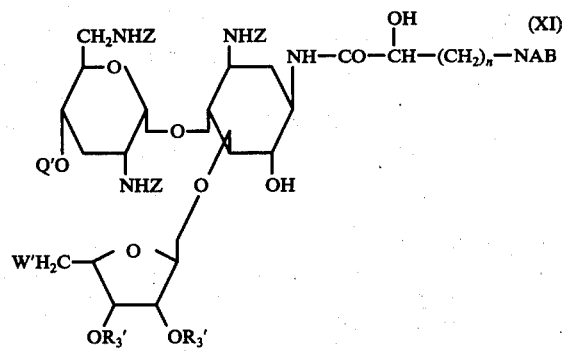

wherein A, B, Z and n are as defined hereinbefore, $R_3'$ is a hydrogen atom or the group $R_3$ as defined hereinbefore, W' is hydroxyl group or the group W as defined herebefore, and Q' is a hydrogen atom or the group Q as defined hereinbefore, reacting the 1-N-acylation product (XI) with an azidating agent, in case the 1-N-acylation product (XI) contains a sulfonyloxy group or a halogeno group as the group W at the 5''-position thereof, whereby the 5''-sulfonyloxy or 5''-halogeno group is replaced by the 5'-azido group, giving the 5''-azidation product derived from the 1-N-acylation product (XI), reducing the 1-N-acylation product (XI) in case this 1-N-acylation product (XI) contains azido group as the group W at the 5''-position thereof, or the above-mentioned 5''-azidation product, whereby the 5''-azido group is converted into 5''-amino group, and simultaneously or subsequently or both removing the residual protecting groups out of the 1-N-acylation product (XI) where W' is hydroxyl group or a group $-OR_3$, or out of the reduction product obtained from the above-mentioned reduction step, to produce the desired product of the formula (I).

In regard to the second aspect process according to the present invention, if desired, this process may further comprise an additional step of reacting the compound (X) or (X') with an azidating agent when the compound (X) or (X') contains a sulfoxyloxy group $-OSO_2R'$ or a halogeno group as the group W at the 5''-position thereof, whereby the 5''-sulfonyloxy or 5-- halogeno group is replaced by 5''-azido group. This additional step is conducted just before the step of hydrolysing the compound (X) or (X') under basic conditions to effect the ring-fission of the 1,6-carbamate ring.

With respect to the 3'-deoxyneamine 1,6-carbamate derivative (IX) which is used as the starting compound for the second aspect process of the present invention, the amino-protecting group Z present therein may be of the same nature as the amino-protecting group Z in the starting 3'-deoxyparomamine 1,6-carbamate derivative (II) for use in the first aspect process of the present invention. When the hydroxyl-protecting group Q for the 4'-hydroxyl group of the starting compound (IX) is an alkanoyl group, it may be, for example, an alkanoyl group of 2–5 carbon atoms, such as acetyl, propionyl, butyryl and valeryl. When the group Q is an aroyl group, it may be, for example, benzoyl, o-nitrobenzoyl, p-nitrobenzoyl, 1-naphthoyl and 2-naphthoyl. When the group Q is an alkoxycarbonyl group, an aryloxycarbonyl group or an aralkoxycarbonyl group, it may generally be represented by a group of the formula — $COOR_7$ where $R_7$ is an alkyl group, an aryl group or an aralkyl group. Suitable examples of an alkoxycarbonyl group for Q include an alkoxycarbonyl group of 1–4 carbon atoms in particular, such as methoxycarbonyl, ethoxycarbonyl, propoxycarbonyl, isopropoxycarbonyl and butoxycarbonyl. Suitable examples of an aryloxycarbonyl group for Q include phenoxycarbonyl. Suitable examples of an aralkoxycarbonyl group for Q include benzyloxycarbonyl, p-methoxybenzyloxycarbonyl, p-ethoxybenzyloxycarbonyl, p-chlorobenzyloxycarbonyl and p-nitrobenzyloxycarbonyl.

In the second aspect process of the present invention, the pentofuranosyl compound (III) or (III') used to be condensed with the starting compound (IX) is very the same as the pentofuranosyl compound (III) or (III') for use in the first aspect process of the present invention. The step of reacting the starting compound (IX) with the pentofuranosyl compound reagent (III) or (III') in the second aspect process of the present invention may be carried out in the same manner as in the corresponding step of the first aspect process of the present invention. Thus, it may take place in a liquid reaction medium. As the reaction medium, there may be employed any organic solvent in which the reactants are at least partially soluble and which is inert to the condensation reaction, such as dichloromethane, chloroform, tetrahydrofuran, dioxane, dimethylformamide, dimethylacetamide, acetonitrile, nitromethane, benzene, toluene and ethylether. The condensation reaction may suitably be carried out in the presence of mercuric cyanide, mercuric bromide, silver carbonate, silver oxide or pyridine in order to promote the reaction. The reaction may be conducted at a temperature of ranging from 0° C to 150° C for a reaction time of 0.5 to 48 hours.

The above condensation step gives the compound of the aforesaid general formula (X) or (X'), which is subsequently subjected to the alkaline hydrolysis step to fission the 1,6-carbamate ring thereof. The resultant ring-fission product so obtained is then subjected to the 1-N-acylation step using an α-hydroxy-α-aminoalkanoic acid (VII), followed by the step for removal of the residual protecting groups. These reaction steps of the second aspect process of the present invention may be worked in the same manner and under the same reaction conditions in the corresponding reaction steps of the first aspect process of the present invention, respectively. In case a sulfonyloxy or halogeno group is present as the group W at the 5''-position of the 1-N-acylation product (XI), however, it is necessary to carry out a reaction step where the 1-N-acylation product (XI) containing a 5''-sulfonyloxy or 5''-halogeno group is reacted with an azidating agent to replace the 5''-sulfonyloxy or 5''-halogeno group by 5''-azido group, as well as a reaction step where the 5''-azido group is reduced into 5''-amino group to give the 5''-amination product, before the step for the removal of the residual protecting groups is carried out. On the other hand, in case azido group is initially present as the group W at the 5"-position of the 1-N-acylation product (XI), it is, of course, necessary to carry out the step of reducing such 1-N-acylation product (XI) containing the 5"-azido group where the 5"-azido group is converted into 5" -amino group to give the 5"-amination product, before the step for the removal of the residual protecting groups takes place. In this way, the desired 1-N-(α-hydroxy-ω-aminoalkanoyl)-3'-deoxy-5-O-pentofuranosylneamine (I) is produced as the desired final product.

The 3'-deoxyparamamine 1,6-carbamate derivative (II) which is employed as the starting compound in the first aspect process of the present invention, as well as the 3'-deoxyneamine 1,6-carbamate derivative (IX) which is employed as the starting compound in the second aspect process of the present invention may be prepared in such a manner that 3'-deoxyparomamine or 3'-deoxyneamine is successively treated with an alkoxycarbonylating, aralkoxycarbonylating or aryloxycarbonylating agent, with a known reagent for the introduction of amino-protecting groups and then with sodium hydroxide or sodium hydride in a similar way to the preparation of such a protected neamine 1,6-carbamate derivative as described in German "Offenlegungsschrift≠ 2350203 published on Apr. 18, 1974 (the corresponding U.S. patent application Ser. No. 402,086 is now issued under U.S. Pat. No. 3,925,354 on Dec. 9, 1975).

Although the starting compound (IX) for use in the second aspect process of the present invention is such one containing a single 1,6-carbamate ring in the molecule thereof, we have further found that the desired compound (I) may also be synthetized starting from such a corresponding 3'-deoxyneamine 1,6-carbamate derivative of a similar chemical structure but containing additionally one carbamate ring formed between the 4'-hydroxyl group and 6'-amino group thereof, through a similar series of reaction steps as stated hereinafter.

According to the third aspect of the present invention, therefore, there is provided a process for the production of a 1-N-(α-hydroxy-ω-aminoalkanoyl)-3'-deoxy-5-O-pentofuranosylneamine of the general formula (I), which compriss the steps of:

reacting a 3'-deoxyneamine 1,6; 4', 6'-dicarbamate derivative of the general formula:

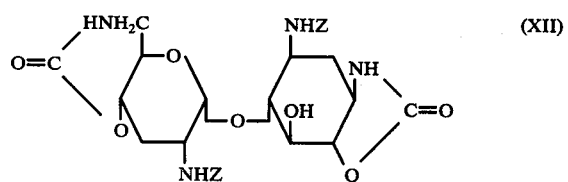
(XII)

wherein Z is an amino-protecting group as defined hereinbefore. with a pentofuranosyl compound of the general formula:

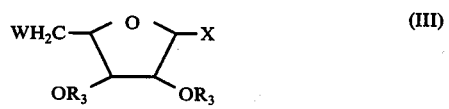
(III)

wherein $R_3$, X and W are as defined hereinbefore, or with a pentofuranosyl ortho-ester compound of the general formula:

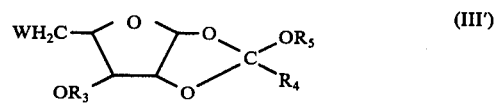
(III')

wherein $R_3$, $R_4$, $R_5$ and W are as defined hereinbefore, to produce a compound of the general formula:

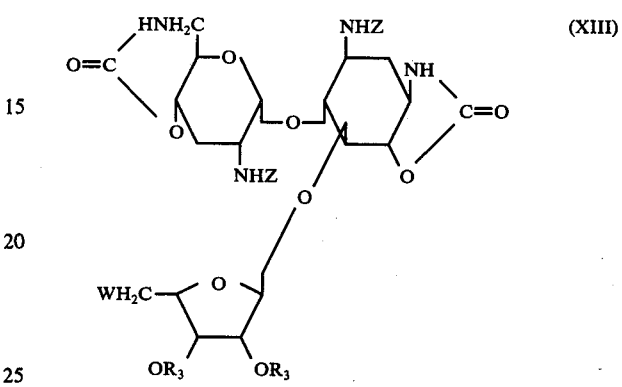
(XIII)

or of the formula:

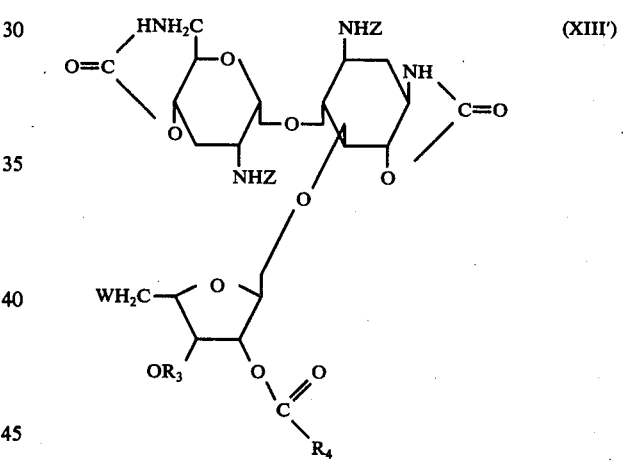
(XIII')

wherein $R_3$, $R_4$, Z and W are as defined hereinbefore, hydrolysing the compound of the formula (XIII) or (XIII') under weakly basic conditions to ring-fission preferentially the 1,6-carbamate ring with liberation of the free 1-amino group and free 6-hydroxyl group and with simultaneous removal of a part or all of the hydroxyl-protecting groups, reacting the resultant ring-fission product bearing the free 1-amino group with an α-hydroxy-ω-aminoalkanoic acid of the general formula:

$$HOOC—CH(OH)—(CH_2)_n—NAB \qquad (VII)$$

wherein n, A and B are as defined hereinbefore, or a functional equivalent of said α-hydroxy-Ω-aminoalkanoic acid to produce a 1-N-acylation product of the general formula:

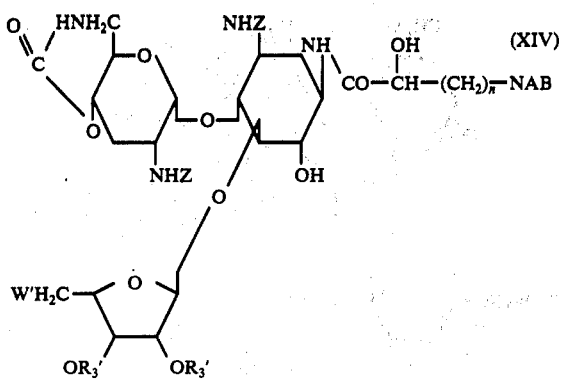

wherein A, B, Z and n are as defined hereinbefore, R₃' is a hydrogen atom or the group R₃ as defined hereinbefore, and W' is hydroxyl group or the group W as defined hereinbefore.

reacting the 1-N-acylation product (XIV) with an azidating agent, in case the 1-N-acylation product (XIV) contains a sulfonyloxy or halogeno group as the group W at the 5''-position thereof, whereby the 5''-sulfonyloxy or 5''-halogeno group is replaced by the 5''-azido group, giving the 5''-azidation product derived from the 1-N-acylation product (XIV), reducing the 1-N-acylation product (XIV) in case the 1-N-acylation product (XIV) contains azido group at the 5''-position thereof, or the above-mentioned 5''-azidation product, whereby the 5''-azido group is converted into the 5''-amino group, giving the 5''-amination product, hydrolysing the 1-N-acylation product (XIV) where W' is hydroxyl group or a group –OR₃, or the above-mentioned 5''-amination product, under basic conditions to ring-fission the 4',6'-carbamate ring thereof, with liberation of free 4'-hydroxyl group and free 6'-amino group, and simultaneously or subsequently or both removing the residual protecting groups from the resulting hydrolysis product of the just above-mentioned hydrolysing step to produce the desired product of the formula (I).

In regard to this third aspect process according to the present invention, if desired, this process may further comprise an additional step of reacting the compound (XIII) or (XIII') with an azidating agent, in case the compound (XIII) or (XIII') contains a sulfonyloxy group —OSO₂R' or a halogeno group as the group W at the 5''-position thereof, whereby the 5''-sulfonyloxy or 5''-halogeno group is replaced by 5''-azido group. This additional step is conducted just before the step of hydrolysing the compound (XIII) or (XIII') under weakly basic conditions to effect the selective ring-fission of the 1,6-carbamate ring.

With the 3'-deoxyneamine 1,6;4',6'-di-carbamate derivative (XII) which is employed as the starting compound in the third aspect process of the present invention, the amino-protecting group Z present therein may be of the same nature as the group Z in the starting 1,6-carbamate compound (II) for use in the first aspect process of the present invention. The pentofuranosyl compound (III) or (III') used to be condensed with the starting 1,6;4',6'-di-carbamate compound (XII) may be the same as the one used in the first aspect process of the present invention. In the third aspect process of the present invention, the step of condensing the starting 1,6;4',6'-di-carbamate compound (IX) with the pentofuranosyl compound (III) or (III') may be conducted in the same manner and under the same reaction conditions as in the step of reacting the starting 1,6-carbamate compound (II) with the pentofuranosyl compound (III) or (III') according to the first aspect process of the present invention. This condensation step gives the compound of the general formula (XIII) or (XIII'), which is subsequently subjected to a hydrolysis step under weakly basic conditions to effect the preferential ring-fission of the 1,6-carbamate ring of this compound. This hydrolysis step may be carried out in such a manner that a solution of the compound (XIII) or (XIII') in an aqueous organic solvent such as aqueous tetrahydrofuran, aqueous dioxane or aqueous methanol is stirred at ambient temperature or below by adding slowly thereto a limited amount of a weakly alkaline reagent such as sodium carbonate or barium hydroxide while the reaction mixture is kept at a pH value in the range of weak alkalinity to slight alkalinity. In this way, the 1,6-carbamate ring can be decomposed or ring-opened preferentially, as the 1,6-carbamate is less stable than the 4',6'-carbamate ring under the alkaline conditions.

According to the third aspect process of the present invention, the reaction of fissioning preferentially the 1,6-carbamate ring of the compound (XIII) or (XIII'') takes place in the above-mentioned alkaline hydrolysis step, with accompanying simultaneous removal of a part or all of such hydroxyl-protecting groups which are cleavable by hydrolysis, so that the 3'-deoxyneamine 4',6'-carbamate derivative containing the free 1-amino group is formed as the ring-fission product. The 3'-deoxyneamine 4',6'-carbamate derivative so formed is then reacted in a next step with an α-hydroxy-ω-amino acid (VII) to effect the 1-N-acylation giving the 1-N-acylation product of the formula (XIV). This 1-N-acylation step may be accomplished in the same manner and under the same reaction conditions as in the corresponding 1-N-acylation step of the second aspect process of the present invention. Immediately after the 1-N-acylation step, the resulting 1-N-acylation product (XIV), that is, the 1-N-acylation 4',6'-carbamate derivative is subjected to a further hydrolysis step under basic conditions to ring-fission the remaining 4',6'-carbamate ring, and this further hydrolysis step may be carried out in the same manner but under stronger reaction conditions as in the step of ring-fissioning the 1,6-carbamate ring of the 6'-azidation product in the first aspect process of the present invention. This further hydrolysis step to effect the fission of the 4',6'-carbamate ring is occasionally accompanied by simultaneous removal of a part or all of the residual protecting groups and is, if necessary, followed by a step of removing all of the remaining protecting groups to give the desired final product (I). In case the 1-N-acylation product (XIV) contains a sulfonyloxy or halogeno group as the group W at the 5''-position thereof, however, it is then necessary to carry out such a reaction step where such 1-N-acylation product (XIV) containing the 5''-sulfonyloxy or 5''-halogeno group is reacted with a azidating agent to replace the 5''-sulfonyloxy or 5''-halogeno group by 5''-azido group, as well as such a reaction step where the 5''-azidation product os derived is reduced to convert the 5''-azido group into 5''-amino group, giving the 5''-amination product, before the step for the removal of the residual protecting groups is effected to give the desired final product (I). On the other hand, in case azido group is present initially as the group W at the 5″-position of the 1-N-acylation product (XIV), it is necessary to conduct the step of reducing the 1-N-acylation product (XIV) bearing the 5″-azido group so that the 5″-azido group is reduced into 5″-amino group to give the 5″-amination product similarly, and this step may be effected before the step for removal of the residual protective groups takes place. All of these reaction steps of the third aspect process of the present invention may be accomplished in the same manner as the corresponding reaction steps of the first and/or second aspect processes of the present invention. In this way, there is equally obtained the 1-N-(α-hydroxy-Ω-aminoalkanoyl)-3′-deoxy-5-0-pentofuranosylneamine of the formula (I) as the desired, final product.

Moreover, we have found that the desired compound of the formula (I) may be synthetized through another route also starting from such a 3′-deoxyneamine 1,6-carbamate derivative which is substantially corresponding to the 3′-deoxyneamine derivative (IX) for use as the starting compound in the second aspect process of the present invention but of which the 6′-amino group has been replaced by 6′-azido group, when a similar series of reaction steps to that of the second aspect process of the present invention is conducted, provided that an additional step of reducing the 6′-azido group into 6′-amino group is introduced at an appropriate stage after the step of condensing with the pentofuranosyl compound (III) or (III′).

According to the fourth aspect of the present invention, therefore, there is provided a process for the production of a 1-N-(α-hydroxy-ω-aminoalkanoyl)-3′-deoxy-5-0-pentofuranosylneamine of the aforesaid general formula (I), which comprises the steps of:

reacting a 6′-azido-6′-deamino-3′-deoxyneamine 1,6-carbamate derivative of the general formula:

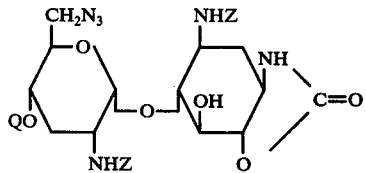
(XV)

wherein Q is a hydroxyl-protecting group as defined hereinbefore, and Z is an amino-protecting group as defined hereinbefore, with a pentofuransoyl compound of the general formula:

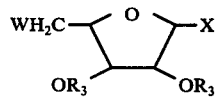
(III)

wherein $R_3$, X and W are as defined hereinbefore, or with a pentofuranosyl ortho-ether compound of the general formula:

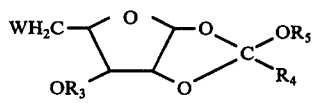
(III′)

wherein $R_3$, $R_4$, $R_5$ and W are as defined hereinbefore, to produce a compound of the general formula:

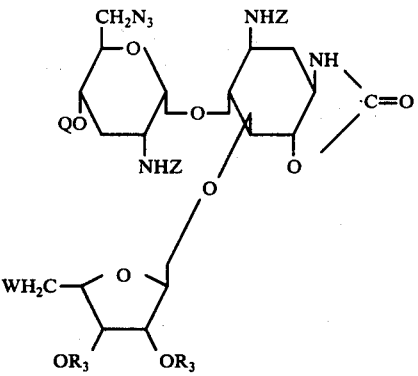
(XVI)

or of the general formula:

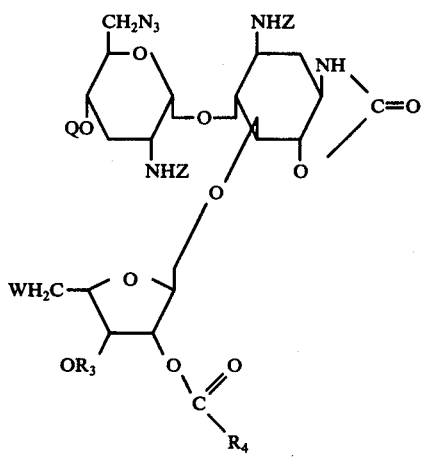
(XVI′)

wherein $R_3$, $R_4$, Z and W are as defined hereinbefore, hydrolysing the compound of the formula (XIV) or (XVI′) under basic conditions to ring-fission the 1,6-carbamate ring with liberation of the free 1-amino group and free 6-hydroxyl group and with simultaneous removal of a part or all of the hydroxyl-protecting groups, reacting the resultant ring-fission product bearing the free 1-amino group with an α-hydroxy-ω-aminoalkanoic acid of the general formula:

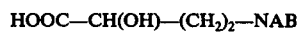

HOOC—CH(OH)—(CH$_2$)$_2$—NAB (VII)

wherein n, A and B are as defined hereinbefore, or a functional equivalent of said α-hydroxy-ω-aminoalkanoic acid to produce a 1-N-acylation product of the general formula:

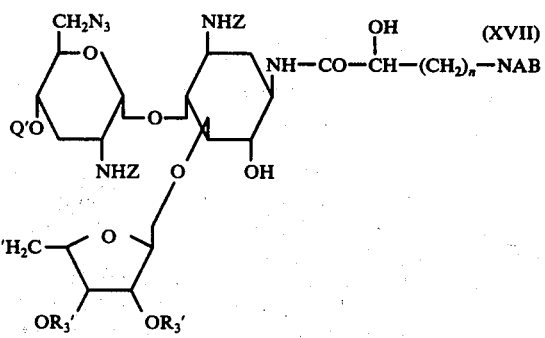
(XVII)

wherein A, B, Z and n are as defined hereinbefore, R₃' is a hydrogen atom or the group R₃ as defined hereinbefore, Q' is a hydrogen atom or the group Q as defined hereinbefore, and W' is hydroxyl group or the group W as defined hereinbefore, reacting the 1-N-acylation product (XVII) with an azidating agent, in case the 1-N-acylation product (XVII) contains a sulfonyloxy or halogeno group for the group W at the 5''-position thereof, whereby the 5''-sulfonyloxy or 5''-halogeno group is replaced by 5''-azido group, giving the 5''-azidation product derived from the 1-N-acylation product (XVII), reducing the 1-N-acylation product (XVII) or the above-mentioned 5''-azidation product, whereby the 6'-azido group is converted into the 6'-amino group, with simultaneous reduction of the 5''-azido group into the 5''-amino group if the 5''-azido group is present, and simultaneously or subsequently or both removing the residual protecting groups from the resulting reduction product to produce the desired product of the formula (I).

In regard to the fourth aspect process according to the present invention, if desired, this process may further comprises an additional step of reacting the compound (XVI) or (XVI') with an azidating agent when the compound (XVI) or (XVI') contains a sulfonyloxy group —$OSO_2R'$ or a halogeno group as the group W at the 5''-position thereof, whereby the 5''-sulfonyloxy or 5''-halogeno group is replaced by 5''-azido group. This additional step is conducted just before the step of hydrolysing the compound (XVI') or (XVI') under basic conditions to effect the ring-fission of the 1,6-carbamate ring.

The 6'-azido-6'-deamino-3'-deoxyneamine 1,6-carbamate derivative (XV) which is used as the starting compound in the fourth aspect process of the present invention may be prepared, for example, by hydrolysing a 3'-deoxyparomamine 1,6-carbamate compound (II) which is employed as the starting compound in the first aspect process of the present invention, in aqueous acetic acid to remove the di-valent hydroxyl-protecting group Y, reacting the resulting product with tosyl chloride to tosylate selectively the 6'-hydroxyl group, and then reacting the 6'-tosyl ester groups with sodium azide to convert it into the 6'-azido group, acylating the free 4'-hydroxyl group with an acylating agent to have the 4'-hydroxyl group protected.

With the 6'-azido compound (XV) which is employed as the starting compound for the fourth aspect process of the present invention, the amino-protecting group Z present therein may be of the same nature as the group Z in the starting 3'-deoxyparaomamine 1,6-carbamate compound (II) used in the first aspect process of the present invention. The hydroxyl-protecting group Q present therein may also be of the same nature as the group Q in the starting 3'-deoxyneamine 1,6-carbamate compound (IX) used in the second aspect process of the present invention. The step of reacting the starting compound (XV) with the pentofuranosyl compound (III) or (III') for condensation may be conducted according to the fourth aspect process of the present invention in the same manner and under the same reaction conditions as in the corresponding condensation step of the second aspect process of the present invention, so that the compound (XVI) or (XVI') is produced. The compound (XVI) or (XVI') is then subjected to a hydrolysis step for the ring-fission of the 1,6-carbamate ring, and this hydrolysis step may be accomplished in the same manner and under the same reaction conditions in the corresponding step of the second aspect process of the present invention.

The ring-fission product bearing the free 1-amino group so formed is then subjected to the successive steps of reacting with an α-hydroxy-ω-amino acid (VII) for the 1-N-acylation, of reducing the 6'-azido group into 6'-amino group and of removing the residual protective groups, which steps all may generally be carried out in the same manner and under the reaction conditions as in the corresponding steps of the first aspect process of the present invention, respectively. In case the 1-N-acylation product (XVII) contains a sulfonyloxy group or a halogeno group as the group W at the 5''-position thereof, however, it is necessary to carry out such a reaction step where such 1-N-acylation product (XVII) containing the 5''-sulfonyloxy or 5''-halogeno group is reacted with an azidating agent to replace the 5''-sulfonyloxy or 5''-halogeno group by 5''-azido group, and this 5''-azidation step may be accomplished in the same manner and under the same reaction conditions as in the corresponding azidation step of the first aspect process of the present invention. This 5''-azidation step may preceed the reduction step for conversion of 6'-azido group into 6'-amino group. When the 1-N-acylation product (XVII) undergoes the reduction step for conversion of 6'-azido group into 6'-amino group, the 5''-azido group may also be reduced into 5''-amino group concurrently, if it is present in the compound (XVII). This is true also when the 5''-azidation product as derived from the 1-N-acylation product initially bearing a 5''-sulfonyloxy or 5''-halogeno group is subjected to the reduction step. In thiw way, the 1-N-(α-hydroxy-ω-aminoalkanoyl)-3'-deoxy-5-O-pentofuranosylneamine of the formula (I) is obtained as the desired final product also according to the fourth aspect process of the present invention.

As the examples of the desired final product of the formula (I) as produced by the processes of the present invention, there may be mentioned the following particular compounds:

1. Compound No. 1: 1N-((RS)-3-amino-2-hydroxy-propionyl)-3'-deoxy-5-O-β-D-xylofuranosylneamine. This is a new compound which is a colorless crystalline powder having no definite melting point. Optical rotation $[\alpha]_D^{20}$ +25.5° (c 1, water).

2. Compound No. 2: 1-n-((S)-3-amino-2-hydroxypropionyl)-3'-deoxy-5-O-β-D-xylofuranosylneamine. This is a new compound which is a colorless crystalline powder having no definite melting point. Optical rotation $[\alpha]_D^{20}$ +21° (c 1, water).

3. Compound No. 3: 1-N-((S)-4-amino-2-hydroxybutyryl)-3'-deoxy-5-O-α-L-arabinofuranosylneamine. This is also a new compound which is a colorless crystalline powder having no definite melting point. Optical rotation $[\alpha]_D^{20}$ +29° (c 1, water).

4. Compound No.4: 1-N-((S)-4-amino-2-hydroxybutyryl)-5-O-(5-amino-5-deoxy-β-D-xylofuranosyl)-3'-doxyneamine. This is a new compound which is a colorless crystalline powder having no definite melting point. Optical rotation $[\alpha]_D^{23}$ +26° (c 1, water).

5. Compound No. 5: 1-N-((S)-4-amino-2-hydroxybutyryl)-3'-deoxy-5-O-β-D-ribofuranosylneamine. This is a compound which is already known as 3'-deoxybutirosin B.

6. Compound No.6: 1-N-((S)-4-amino-2-hydroxybutyryl)-3'-deoxy-5-O-β-D-xylofuranosylneamine. This is a compound which is already known as 3'-deoxybutirosin A.

These particular compounds, that is, 1-n-(α-hydroxy-ω-aminoalkanoyl)-3'-deoxy-5-O-pentofuranosylneamines according to the aforesaid general formula (I) have useful antibacterial activity against a wide variety of bacteria, including gram-negative bacteria and gram-positive bacteria. Antibacterial spectra of these compounds are shown in Table 1 below. The minimum inhibitory concentration (M.I.C.) (mcg/ml) of these compounds against various organisms was determined by a standard serial dilution method at an incubation temperature of 37° C, the estimation being made after 18 hours incubation or each test organism, except that the incubation time was 48 hours for Mycobacterium smegmatis. The incubation medium used was nutrient agar.

amino-5-deoxy-β-D-xylofuranosyl group when $n$ is 2, and a pharmaceutically acceptable acid-addition salt thereof.

The new compounds of the formula (I') according to the fifth aspect of the present invention are active aginst gram-positive bacteria, gram-negative bacteria and acid-fast bacteria and are of low toxicity, as they exhibit an $LD_{50}$ value of more than 200 mg/kg upon intravenous injection in mice. The new compounds of the formula (I') may be administered orally, intraperitoneally, intravenously or intramuscularly using any pharmaceutical form known to the art for such administration and in a similar manner to kanamycins. Examples of pharmaceutical forms for oral administration ar powders, capsules, tablets, syrup, and the like. Suitable doses of the present compounds for effective treatment of bacterial infections are in a range of 0.25 to 3 g per person a day when it is given orally. The new com- Table 1

| Test Organisms | | Compound No. 1 | Compound No. 2 | Compound No. 3 | Compound No. 4 | Compound No. 5 (3'-deoxybutirosin B) | Compound No. 6 (3'-deoxybutirosin A) |
|---|---|---|---|---|---|---|---|
| | | M.I.C. (mcg/ml) | | | | | |
| Staphylococcus aureus | FDA 209P | 3.12 | 1.56 | 0.39 | 0.39 | 0.39 | 0.39 |
| Sarcina lutea | PCI 1001 | 25 | 25 | 25 | 3.12 | 25 | 25 |
| Bacillus subtilis | B-558 | 1.56 | 0.78 | 0.2 | 0.2 | <0.2 | 0.2 |
| Klebsiella pneumoniae | PCI 602 | 1.56 | 1.56 | 0.39 | 0.39 | 0.39 | 0.39 |
| " | Type 22, No. 3038 | 1.56 | 1.56 | 0.39 | 0.39 | 0.78 | 0.39 |
| Salmonella typhosa | T-63 | 1.56 | 0.78 | 0.78 | 0.2 | 0.39 | 0.78 |
| Escherichia coli | NIHJ | 1.56 | 0.78 | 0.78 | 0.2 | 0.78 | 0.78 |
| " | K-12 | 1.56 | 0.39 | 0.39 | 0.2 | 0.2 | 0.39 |
| " | K-12 ML 1629 | 1.56 | 1.56 | 0.39 | 0.39 | 0.39 | 0.39 |
| " | K-12 ML 1630 | 3.12 | 1.56 | 0.78 | 0.78 | 1.56 | 0.78 |
| " | K-12 ML 1410 | 3.12 | 3.12 | 0.78 | 0.78 | 0.78 | 1.56 |
| " | K-12 ML 1410 R81 | 6.25 | 3.12 | 1.56 | 0.78 | 0.78 | 1.56 |
| " | K-12 LA 290 R55 | 3.12 | 0.78 | 1.56 | 0.39 | 0.78 | 0.78 |
| " | K-12 LA 290 R56 | 3.12 | 0.78 | 0.39 | 0.78 | 0.39 | 0.39 |
| " | K-12 LA 290 R64 | 1.56 | 0.78 | 0.2 | 0.39 | 0.2 | 0.2 |
| " | K-12 W677 | 1.56 | 0.78 | 0.39 | 0.39 | 0.39 | 0.39 |
| " | K-12 JR66/W677 | 3.12 | 0.78 | 1.56 | 0.2 | 1.56 | 0.39 |
| Pseudomonas aeruginosa | A3 | 6.25 | 3.12 | 0.78 | 0.39 | 3.12 | 3.12 |
| " | No. 12 | 12.5 | 12.5 | 12.5 | 3.12 | 25 | 25 |
| " | GN 315 | >100 | >100 | >100 | >100 | >100 | >100 |
| " | TI-13 | 25 | 25 | 25 | 3.12 | 25 | 25 |
| " | 99 | 12.5 | 12.5 | 6.25 | 3.12 | 12.5 | 12.5 |
| Proteus rettgeri | GN 311 | 12.5 | 6.25 | 3.12 | 3.12 | 3.12 | 3.12 |
| " | GN 466 | 3.12 | 1.56 | 0.78 | 0.78 | 0.78 | 0.78 |
| Mycobacterium smegmatis | ATCC 607 | 0.39 | 0.39 | 0.2 | 0.2 | <0.2 | 0.2 |

As some specific compounds amongst the compounds which are represented by the aforesaid general formula (I) as produced by the above-mentioned processes of the present invention are new compounds as stated above, there is provided according to a fifth aspect of the present invention as a new compound a 1N-(α-hydroxy-ω-aminoalkanoyl)-3'-deoxy-5-0-pentofuranosylneamine of the following general formula (I'):

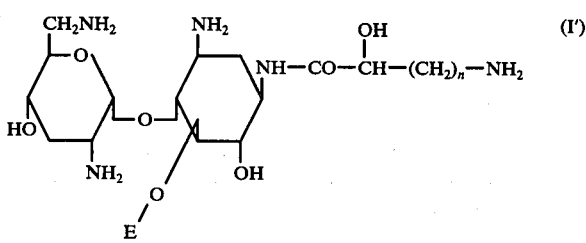

wherein E is β-D-xylofuranosyl group, α-L-arabinofuranosyl group or 5-amino-5-deoxy-β-D-xylofuranosyl group, and $n$ is an integer of 1 or 2, provided that E is β-D-xylofuranosyl group when $n$ is 1 and provided that E is α-L-arabinofuranosyl or 5- pounds of the present invention may also be administered by invravenous injection at a dosage of 50–300 mg person twice to four times a day. Examples of the pharmaceutically acceptable acid-addition salt of the new compound of the formula (I') according to the present invention include the hydrochloride, sulfate, phosphate, nitrate, acetate, maleate, fumarate, succinate, tartarate, oxalate, citrate, methanesulfonate, ethanesulfonate and the like.

According to a sixth aspect of the present invention, there is provided an antibacterial pharmaceutical composition for treating bacterial infections in a living animal, comprising an antibacterially effective amount of a compound of the above general formula (I') or a pharmaceutically acceptable acid-addition salt thereof, in combination with a pharmaceutically acceptable carrier therefor.

This invention is further illustrated by way of the following Examples, in which Examples 1 to 3 represent the first aspect process of this invention, Examples 4 to 6 represent the second aspect process, Example 7 represents the third aspect process, Examples 8 to 12 represent the fourth aspect process of this invention and Examples 13 to 21 illustrate some examples of the preparation of the starting materials to be used for the processes of this invention

DESCRIPTION OF THE PREFERRED EMBODIMENTS

EXAMPLE 1 a. Preparation of 4',6'-O-benzylidene-3,2'-di-N-benzyloxycarbonyl-3'-deoxy-5-O-(2,3,5-tri-O-p-nitrobenzyl-β-D-rifofuranosyl) paromamine 1,6-carbamate of the formula:

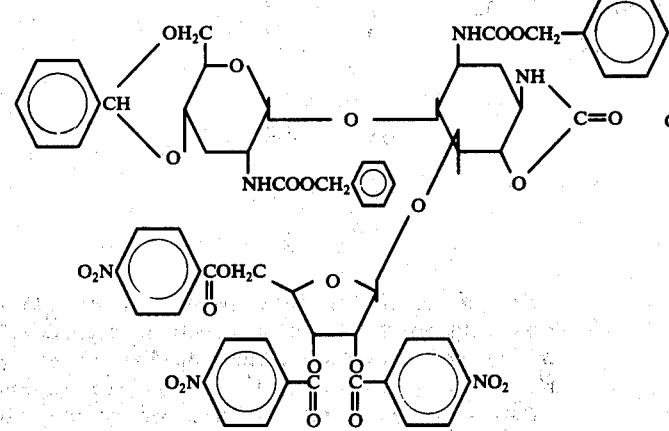

4',6'-0-benzylidene-3,2'-di-N-benzyloxycarbonyl-3'-deoxyparomamine 1,6-carbamate (508 mg) which was prepared as in Example 13 given later and which has the formula:

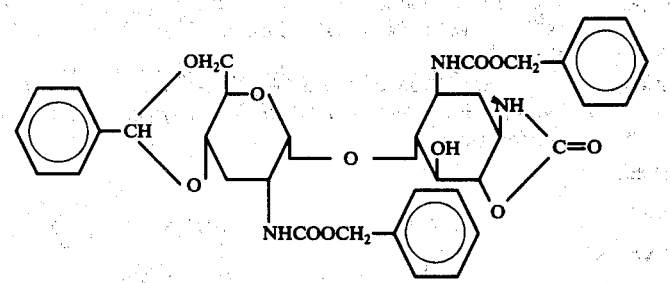

was suspended in anhydrous dichloromethane (15 ml.), to which were then added anhydrous calcium sulfate (3g) and mercuric cyanide (1 g) and thereafter added 2,3,5-tri-O-(p-nitrobenzoyl)-O-ribofuranosyl bromide (1.5 g) which was prepared as in Example 20, and the mixture was vigorously stirred overnight to effect condensation reaction. The insoluble matters in the reaction mixture were filtered off and washed well with dichloromethane. The filtrate was combined with the washing and the mixture thus combined was washed with a saturated solution of sodium hydrogen carbonate and water, successively, and dried over anhydrous sodium sulfate and then subjected to distillation to remove the solvent. The distillation residue was purified by silica-gel column chromatography using chloroformethyl acetate (3:1 by volume) as developer. The eluate was collected in 3 ml-fractions, and such fractions containing the titled compound were combined together and concentrated to dryness.

Yield 625 mg; $[\alpha]_D^{20} + 26°$ (c 1, chloroform)
Elementary analysis:

Calculated for $C_{62}H_{56}N_6O_{24}$ : C 58.67; H 4.45; N 6.62%

Found : C 58.61; H 4.38; N 6.58%.

b. Preparation of 3,2'-di-N-benzyloxycarbonyl-3'-deoxy-5-0-(2,3,5-tri-O-p-nitrobenzoyl-β0-D-ribofuranosyl) paromamine 1,6-carbamate of the formula:

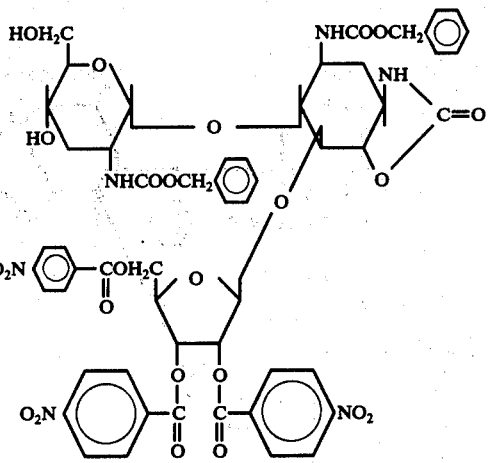

The compound obtained in the step (a) above (500 mg) was dissolved in a 70% aqueous acetic acid and the solution was heated at 80° C for one hour. The solvent was distilled off under a reduced pressure and the residue was dissolved in chloroform. The chloroform solution was washed with water, dried over anhydrous sodium sulphate and concentrated to remove the solvent, affording the titled compound as solid. Yield 380 mg.

c. Preparation of 3,2'-di-N-benzyloxycarbonyl-3'-deoxy-5-0 -(2,3,5tri-O-p-nitrobenzoyl-β-D-ribofuranosyl)-6'-O-tosylparamamine 1,6-carbamate of the formula:

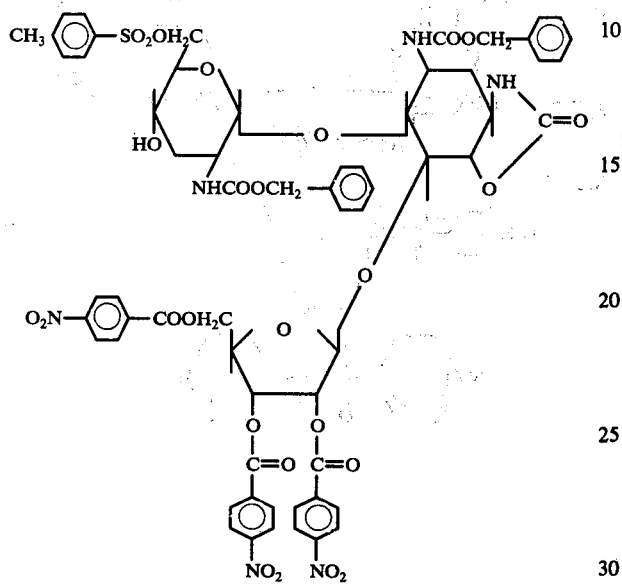

The compound obtained in the step (b) above (750 mg) was dissolved in pyridine (15 ml), to which was added at −10° C p-toluenesulfonyl chloride and the mixture was allowed to stand overnight at −10° C. A small amount of water was added to the solution, which was then concentrated to give a syrup. The syrup was dissolved in chloroform, and the solution was washed, in turn, with 0.4 N potassium hydrogen sulfate solution, saturated sodium hydrogen carbonate solution and water, dried over anhydrous sodium sulfate and concentrated to dryness. The solid residue was purified by chromatography on silica-gel column using chloroform-methyl acetate (3:1 by volume) as developer. The eluate was collected in 3 ml-fractions, and the fractions containing the titled compound were combined together and concentrated to dryness. Yield 633 mg; $[\alpha]_D^{20}$ + 4° (c 0.4, chloroform)

Elementary analysis: Calculated for $C_{62}H_{58}N_6O_{26}S$ : C 55.77; H 4.38; N 6.29; S 2.40% Found : C 55.63; H 4.29; N 6.03; S 2.18%.

d. Preparation of 6'-azido-3,2'-di-N-benzyloxycarbonyl-3α,6'dideoxy-5-O-(2,3,5-tri-O-p-nitrobenzoyl-β-D-ribofuranosyl)paromamine 1,6-carbamate of the formula:

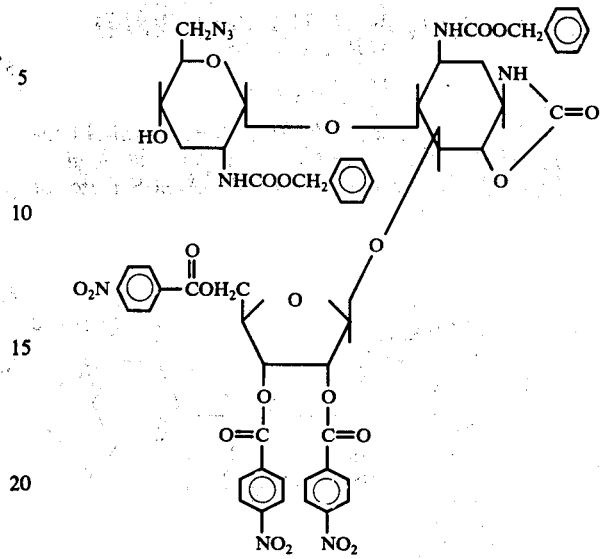

The compound obtained in the step (c) above (627 mg) was dissolved in anhydrous dimethylformamide (12 ml), to which was added sodium azide (500 mg) and the mixture was stirred at 60° C for 7 hours. The reaction mixture was filtered and the filtrate was distilled off under a reduced pressure. The residue was well washed with water, dried and dissolved in dioxane. The solution was filtered and the filtrate was concentrated by distillation to remove the solvent, affording the titled compound as solid. Yield 430 mg; $[\alpha]_D^{20}$ + 6.5° (c 0.8, chloroform)

Elementary analysis: Calculated for $C_{55}H_{51}N_9O_{23}$ : C 54.77; H 42.26; N 10.45%, Found : C 54.62; H, 4.11; N 10.77%.

e. Preparation of 6'-azido-3,2'-di-N-benzyloxycarbonyl-3',6'-dideoxy-5-O-β-D-ribofuranosylparomamine of the formula:

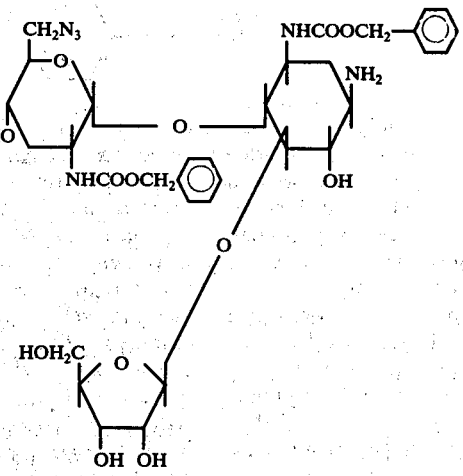

The compound obtained in the step (d) above (410 mg) was dissolved in dioxane (20 ml). The solution was heated to 60° C, to which was slowly added 0.1 N barium hydroxide solution over 3 hours. Carbon dioxide was blown into the solution to deposit a precipitate. The precipitate was filtered off, leaving the filtrate which was then concentrated to dryness. The solid residue was dissolved in dioxane and the solution was filtered. The filtrate was then concentrated to dryness, affording the titled compound as a solid. Infrared spectrum of this compound revealed absorption bands at 2100 cm$^{-1}$ (azido group) and 1700 cm$^{-1}$.

f. Preparation of 6'-azido-3,2'-di-N-benzyloxycarbonyl-1-N-((S)-4-benzyloxycarbonylamino-2-hydroxybutyryl)-3',6'-dideoxy-5-O-$\beta$-D-ribonfuranosyl-paromamine of the formula:

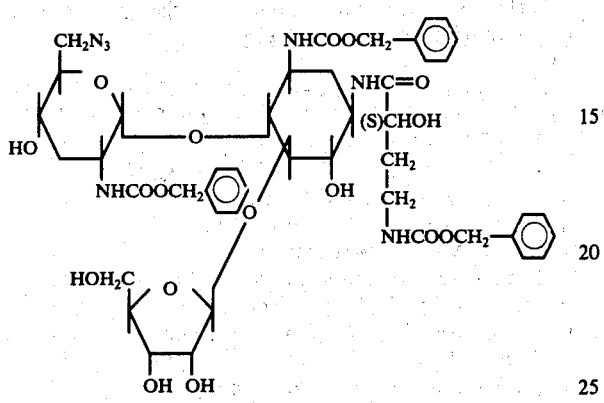

The compound obtained in the step (e) above (50 mg) was dissolved in tetrahydrofuran (0.8 ml), to which were added N-hydroxy-succinimide ester of (S)-4-benzyloxycarbonylamino-2-hydroxybutyric acid (32 mg) and triethylamine (10 mg) and the mixture was allowed to cause 1-N-acylation reaction at room temperature for one hour. The reaction mixture was filtered and the filtrate was concentrated to dryness. The residue was dissolved in chloroform and the solution was washed with 0.4 N potassium hydrogen sulfate and then with saturated sodium hydrogen carbonate solution and dried over anhydrous sodium sulfate.

After filtration, the filtrate was concentrated to dryness, and the residue was developed by chromatography on silica-gel column using chloroform-methanol (10:1 by volume) as developer. The eluate was collected in 3 ml-fractions, and fractions containing the titled compound were combined together and concentrated to dryness, affording the titled compound. Yield 24 mg; $[\alpha]_D^{22} + 18.5°$ (c 0.3, chloroform)

Elementary analysis: Calculated for $C_{45}H_{57}N_7O_{17}$ : C 55.84; H 5.94; N 10.13%, Found : C 55.62; H 5..81; N 9.95%.

g. Preparation of the final compound, 1-N-((S)-4-amino-2-hydroxybutyryl)-3'-deoxy-5-O-$\beta$-D-ribofuranosylneamine of the formula:

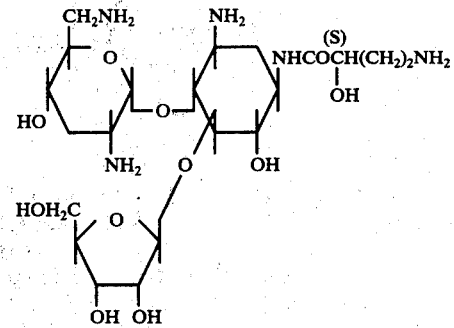

The compound obtained in the step (f) above (34 mg) was dissolved in dioxane (0.6 ml), to which were added water (0.4 ml) and then acetic acid (one drop), and the mixture was subjected to reduction with hydrogen in the presence of palladium black as catalyst. The reaction mixture was filtered and the filtrate was concentrated to dryness, affording powder. The powder was dissolved in water and the solution was chromatographed in a column of a weak cation-exchanger, CM-Sephadex C-25 (a commercial product of Pharmacia Co., Sweden) by developing with aqueous ammonia while increasing the ammonia concentration from 0.1 N to 0.4 N. The active fractions containing the desired compound were collected and concentrated, giving the titled compound as a solid. Yield 10 mg; $[\alpha]_D^{23} + 26.3°$ (c 1, water )

EXAMPLE 2 a. Preparation of 3,2'-di-N-benzyloxycarbonyl-4',6'-O-cyclohexylidene-3'-deoxy-5-O-(2,3,5-tri-O-p-nitrobenzoyl-$\beta$-D-ribofuranosyl) paromamine 1,6-carbamate of the formula:

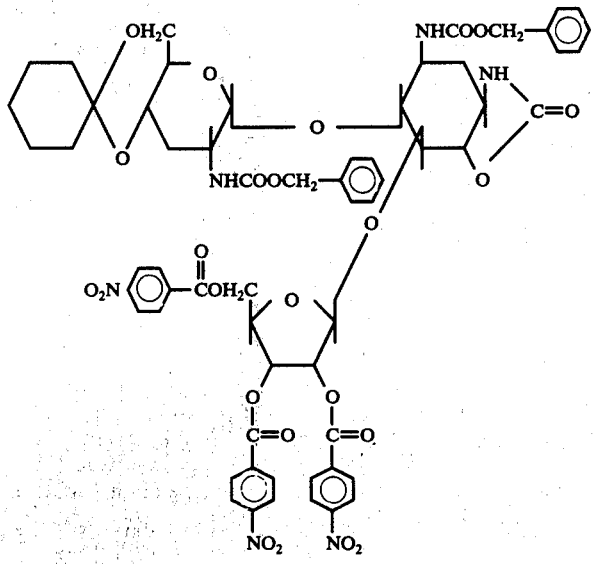

3,2'-Di-N-benzyloxycarbonyl-4',6'-O-cyclohexylidene-3'-deoxyparomamine 1,6-carbamate (505 mg) which was prepared as in Example 15 given later and which has the formula:

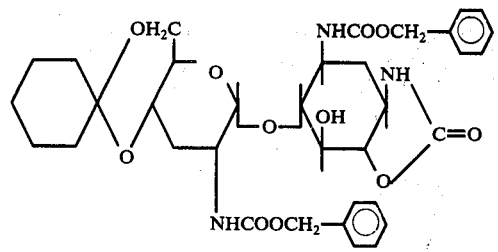

was suspended in anhydrous dichloromethane (15 ml). This was reacted with 2,3,5-tri-O-(p-nitrobenzoyl)-D-ribofuranosyl bromide and after-treated in the same manner as in Example 1 (a) to give the titled compound as a solid. Yield 611 mg; $[\alpha]_D^{20} + 10°$ (c 1, chloroform)

Elementary analysis: Calculated for $C_{61}H_{60}N_6O_{24}$: C 58.09; H 4.80; N 6.66% Found : C 57.83; H 4.92; N 6.58%.

b. The compound obtained in the step (a) above (500 mg) was dissolved in 70% aqueous acetic acid and the solution was heated at 85° C for 10 hours. The reaction mixture was treated in the same manner as in Example 1 (b), affording the compound, 3,2'-di-N-banzyloxycarbonyl-3'-deoxy-5-O-(2,3,5-tri-O-p-nitrobenzoyl-β-D-ribofuranosyl) paromamine 1,6-carbamate. Yield 350 mg;

The compound thus obtained was treated in the same manner as in Example 1 (c), (d), (e), (f) and (g), affording as the final product 1-N-((S)-4-amino-2-hydroxybutyryl)-3'-deoxy-5-O-β-D-ribofuranosylneamine.

EXAMPLE 3 a. Preparation of 5-O-(2,3,-di-O-acetyl-5-O-(p-toluene-sulfonyl)-β-D-xylofuranosyl)-3,2'-di-N-benzyloxycarbonyl-4',6'-O-cyclohexylidene-3'-deoxyparomamine 1,6-carbamate of the formula:

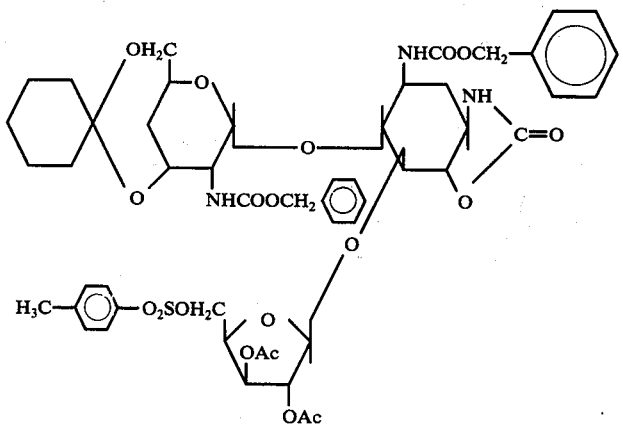

3,2'-Di-N-benzyloxycarbonyl-4',6'-O-cyclohexylidene-3'-deoxyparomamine 1,6-carbamate (1.36 g) which is the same as the compound used in Example 2 (a) was suspended in anhydrous dichloromethane (25 ml), to which were added anhydrous calcium sulfate (2.6 g) and mercuric cyanide (2.6 g) and then added 2,3-di-O-acetyl-5-O-(p-toluenesulfonyl)-D-xylofuranosyl bromide (2.9 g) which was prepared as in Example 21 given later. The mixture was vigorously stirred overnight to effect condensation reaction. The insoluble matters were filtered off and washed well with dichloromethane. The filtrate was combined with the said washing, washed with water, dried over anhydrous sodium sulfate and subjected to distillation to remove the solvent. The resulting residue was purified by chromatography on silica-gel column using chloroform-ethanol (30:1 by volume) as developer. The eluate was collected in 3 ml fractions, and fractions containing the titled compound wire combined together and concentrated to dryness. Yield 1.28 g; $[\alpha]_D^{23} + 8°$ (c 1, chloroform)

Elementary analysis: Calculated for $C_{51}H_{61}N_3O_{19}S$: C 58.22; H 5.84; N 3.99; S 3.05%, Found: C 58.13; H 5.59; N 3.83; S 2.88%.

b. Preparation of 5-O-[2,3-di-O-acetyl-5-O-(p-toluenesulfonyl)-β-D-xylofuranosyl]-3,2'-di-N-benzyloxycarbonyl-4',6'-O-cyclohexylidene-3'-deoxyparamamine 1,6-carbamate.

The compound obtained in the step (a) above (1.05 g) was dissolved in 70% acetic acid and the resulting solution was heated at 65° C for 24 hours. The reaction mixture was then treated in the same manner as in Example 1 (b) to yield the titled compound. Yield 920 mg; $[\alpha]_D^{23} + 13°$ (c 1, chloroform)

c. Preparation of 5-O-(2,3-di-O-acetyl-5-O-p-toluenesulfonyl -β-D-xylofuranosyl)-3,2'-di-N-benzyloxycarbonyl-3'-deoxy-6'-O-p-toluenesulfonyl-paromamine 1,6-carbamate The compound obtained in the step (b) above (1.01 g) was dissolved in pyridine (20 ml), to which was then added p-toluenesulfonyl chloride (690 mg) under cooling at $-10°$ C and the mixture was allowed to stand overnight at $-10°$ C. The reaction mixture was then treated in the same manner as in Example 1 (c). The purification of the product was effected by chromatography on silica-gel column using chloroform-ethanol (30:1 volume) as developer. The eluate was collected in 3 ml fractions and fractions containing the titled compound were combined together and concentrated to dryness, affording the titled compound. Yield 791 mg; $[\alpha]_D^{23} + 5°$ (c 1, chloroform)

Elementary analysis: Calculated for $C_{52}H_{59}N_3O_{21}S_2$: C 55.46; H 5.28; N 3.73; S 5.69%, Found: C 55.36; H 5.31; N 3.54; S 5.78%.

d. Preparation of 5-O-(2,3di-O-acetyl-5-azido-5-deoxy-β-D-xylofuranosyl)-6'-azido-3,2'-di-N-benzyloxycarbonyl-3',6'-di-deoxyparomamine 1,6-carbamate of the formula:

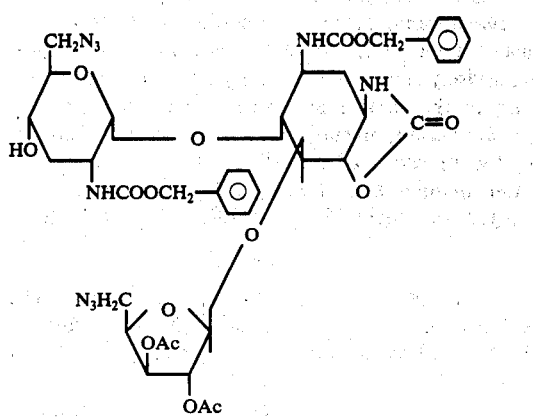

The compound obtained in the step (d) above (563 mg) was dissolved in anhydrous dimethylformamide (11 ml), to which was then added sodium azide (280 mg) and the resulting mixture was stirred at 60° C for 6 hours. The reaction mixture was then treated in the same manner as in Example 1 (d) to give the titled compound. Yield 417 mg; $[\alpha]_D^{23}$ + 10° (c 1, chloroform)

Elementary analysis:
Calculated for $C_{38}H_{45}N_9O_{15}$ : C 52.59; H 5.23; N 14.53% Found: C 52.30; H 5.22; N 14.65%.

e. Preparation of 5-O-(5-azido-5-deoxy-β-D-xylofuranosyl)-6'-azido-1-N-((S)-4-benzyloxycarbonylamino-2-hydroxybutyryl)-3,2'-di-N-benzyloxycarbonyl-3',6'-di-deoxyparomamine of the formula:

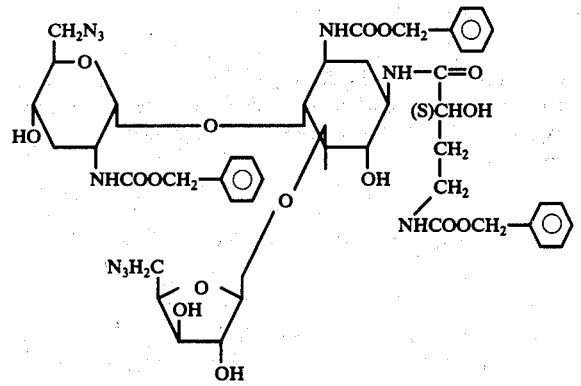

The compound obtained in the step (d) above (260 mg) was dissolved in dioxane (12 ml), to which was slowly added 0.1 N barium hydroxide solution (15 ml) over 2 hours at 60° C. Carbon dioxide was then blown into the mixture whereby precipitation occurred. The precipitate thus deposited was filtered off and the filtrate was concentrated to dryness. The solid matter thus obtained was dissolved in dioxane and the solution was filtered and the filtrate was concentrated. The residue obtained was dissolved in tetrahydrofuran (3 ml), to which was added triethylamine (50 mg) and then added N-hydroxysuccinimide ester of (S)-4-benzyloxycarbonylamino-2-hydroxybutyric acid (157 mg) under ice-cooling and the mixture was allowed to cause reaction at room temperature for 3 hours. The reaction mixture was then treated and purified in the same manner as in Example 1(f). The eluate from the column chromatography was collected in 3 ml fractions and fractions containing the titled compound were combined together and concentrated to dryness, giving the titled compound. Yield 185 mg; $[\alpha]_D^{23}$ +11° (c 1, chloroform)

Elementary analysis Calculated for $C_{45}H_{56}N_{10}O_{16}$: C 54.43; H 5.68; N 14.11% Found: C 54.39; H 5.53; N 13.90%.

f. Preparation of the final compound, 1-N-((S)-4-amino-2-hydroxybutyryl)-5-O-(5-amino-5-deoxy -β-D-xylofuranosyl)-3'-deoxyneamine of the formula:

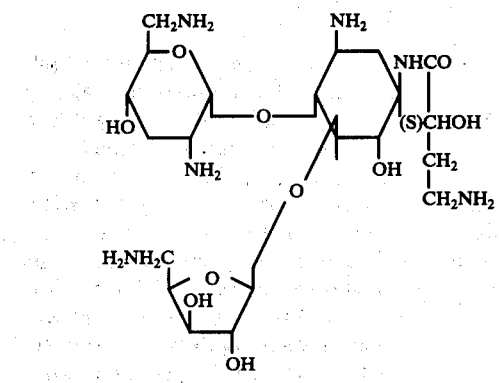

The compound obtained in the step (e) above (99 mg) was dissolved in dioxane (2 ml), to which were then added water (0.5 ml) and acetic acid (2 drops) and the mixture was subjected to reduction with hydrogen in the presence of palladium black as catalyst. The reaction mixture was then treated in the same manner as in Example 1(g). The active fractions containing the desired compound derived from the chromatography were collected and concentrated, yielding the titled compound. Yield 38 mg; $[\alpha]_D^{23}$ +26° (c 1, water).

EXAMPLE 4 a. Preparation of 5-O-(2,3,5-tri-O-benzoyl-β-D-xylofuranosyl)-3,2',6'-tri-N-benzyloxycarbonyl-3'-deoxy-4'-O-α-naphthoylneamine 1,6-carbamate of the formula:

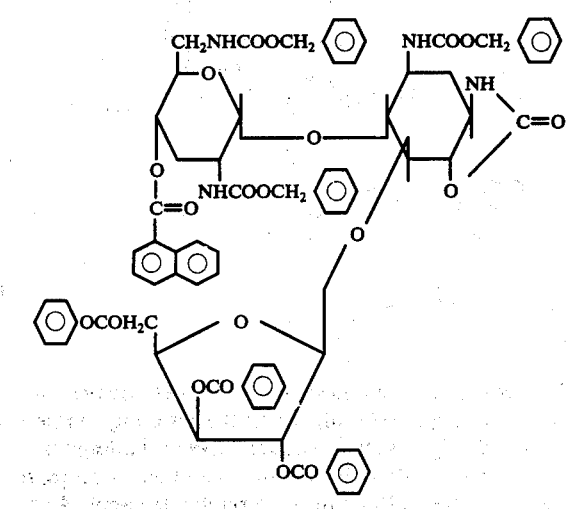

3,2',6'-tri-N-benzyloxycarbonyl-3'-deoxy-4'-O-α-naphthoylneamine 1,6-carbamate (83 mg) which was prepared as in Example 16 given later and which has the formula:

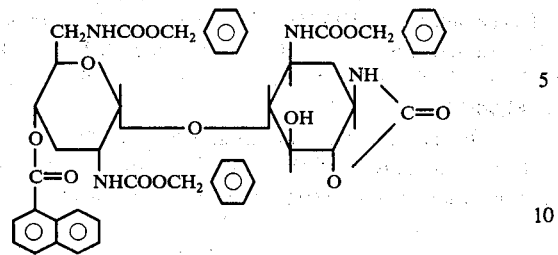

was suspended in anhydrous dichloromethane (1 ml) and to the suspension were added anhydrous calcium sulfate (400 ml), mercuric cyanide (170 mg) and then a solution of tri-O-benzoyl-D-xylofuranosyl bromide (0.3 ml) in anhydrous dichloromethane (2 ml) under stirring. The mixture was vigorously stirred overnight to effect the reaction. The reaction mixture was filtered to remove insoluble matters therefrom and the latter was well washed with dichloromethane. The filtrate was combined with the said washing and the mixture was washed with saturated sodium hydrogen carbonate solution and then with water, dried over anhydrous sodium sulfate and subjected to distillation to remove the solvent. The residue as purified by chromatography on silica-gel column using chloroform-ethyl acetate (2:1 by volume). The eluate was collected in 1 ml fractions and fractions containing the desired compound were combined together and concentrated to dryness, affording the titled compound. Yield 78 mg; $[\alpha]_D^{20}$ +16.3° (c 1, chloroform)

Elementary analysis: Calculated for $C_{74}H_{68}N_4O_{20}$: C 66.66; H 5.14; N 4.20% Found: C 66.46; H 5.38; N 4.19%.

b. Preparation of 3,2′,6′-tri-N- benzyloxycarbonyl-3′,6′-dideoxy-5-O-β-D-xylofuranosylparomamine of the formula:

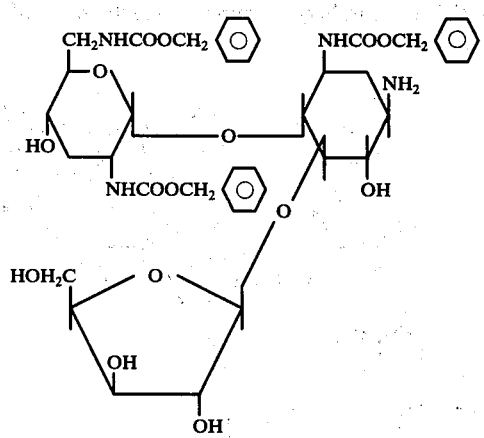

The compound obtained in the step (a) above was dissolved in dioxane (3 ml) and to the resulting solution heated to 60° C was slowly added 0.1N barium hydroxide solution (3.3 ml) under stirring over 3 hours. Carbon dioxide was then blown into the mixture whereby precipitation occurred. The precipitate was filtered off and the filtrate was concentrated to dryness. The solid residue was dissolved in dioxane and the solution was filtered. The filtrate was concentrated to give the titled compound. Yield 45 mg.

c. Preparation of the final compound, 1-N-((S)-4-amino-2-hydroxybutyryl)-3′-deoxy-5-O-β-D-xylofuranosylneamine The compound obtained in the step (b) above (40 mg) was reacted with N-hydroxysuccinimide ester of (S)-4-benzyloxycarbonylamino-2-hydroxybutyric acid (22 mg) in the same manner as in Example 1(f) and the product was then subjected to reduction with hydrogen in the presence of palladium black as catalyst in the same manner as in Example 1(g), affording the titled compound. Yield 28 mg; $[\alpha]_D^{20}$ +22° (c 1, water)

EXAMPLE 5 a. Preparation of 5-O-2,3,5-tri-O-benzoyl-β-D-xylofuranosyl)-3′-deoxy-3,2′,6′-tri-N-ethoxycarbonyl-4′-O-naphthoylneamine 1,6-carbamate of the formula:

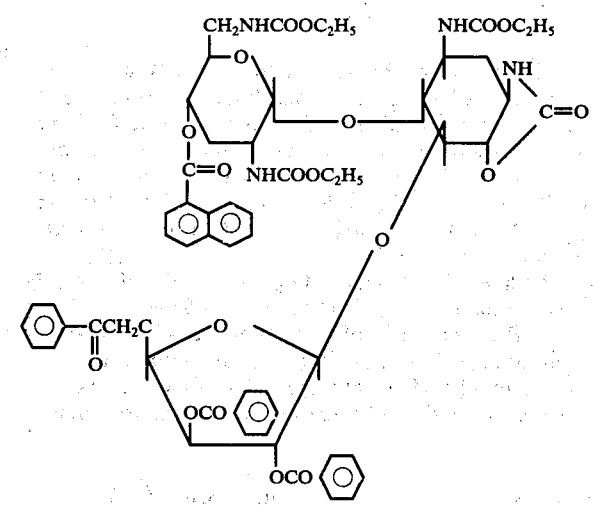

3′-deoxy-3,2′,6′-tri-N-ethoxycarbonyl-4′-O-α-naphthoylneamine 1,6-carbamate (75 mg) which was prepared as in Example 17 given later and which has the formula:

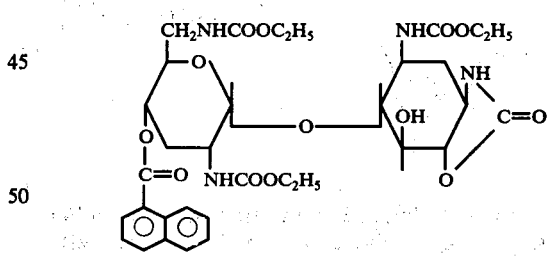

was suspended in anhydrous dichloromethane (1 ml) and reacted with tri-O-benzoyl-D-xylofuranosyl bromide (0.3ml) under the same conditions and in the same manner as in Example 4(a). The reaction mixture was after-treated and purified in the same manner as in Example 4(a). The eluate from the column chromatography was collected in 1 ml fractions and fractions containing the desired compound were combined together and concentrated to dryness, affording the titled compound. Yield 77 mg; $[\alpha]_D^{20}$ +18° (c 1, chloroform)

b. Preparation of 3′-deoxy-3,2′,6′-tri-N-ethoxycarbonyl-5-O-β-D-xylofuranosylneamine The compound obtained in the step (a) above (55 mg) was dissolved in dioxane (3 ml), and to the solution was slowly added 0.1N barium hydroxide solution (3.3 ml)

over 3 hours under stirring. Carbon dioxide was then blown into the mixture, whereby precipitation occurred. The precipitate was filtered off and the filtrate was evaporated to dryness. The solid residue was dissolved in dioxane and the solution was filtered and concentrated, affording the titled compound. Yield 30.5 mg;

c. Preparation of 3'-deoxy-3,2',6'-tri-N-ethoxycarbonyl-1-N-((S)-2-hydroxy-4-phthaloylaminobutyryl)-5-O-β-D-xylofuranosylneamine of the formula:

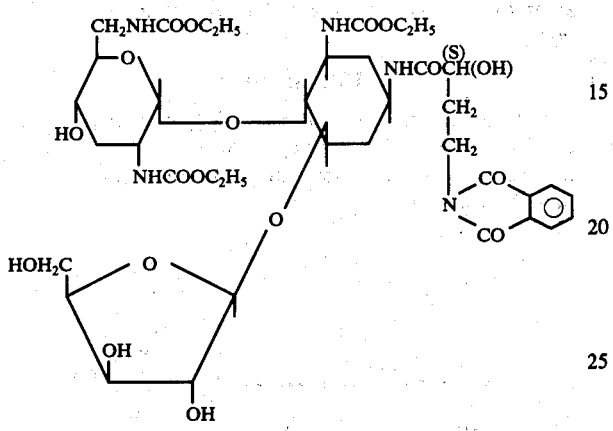

The compound obtained in the step (b) above (40 mg) was dissolved in tetrahydrofuran, and to the solution was added an active ester which had previously been prepared by reacting (S)-2-hydroxy-4-phthaloylamino butyric acid (25 mg), N-hydroxysuccinimide (22 mg) and dicyclohexylcarbimide (22 mg) together in anhydrous tetrahydrofuran, and the resulting mixture was stirred overnight at room temperature. The precipitate thus deposited was filtered off and the filtrate was concentrated to give a solid containing the desired compound. This solid was purified by chromatography on silica-gel column using chloroform-methanol (10:1 by volume) as developer. The eluate was collected in 1 ml fractions and fractions containing the desired compound were combined together and concentrated to dryness, affording the titled compound. Yield 13 mg; $[\alpha]_D^{20}$ +19° (c 0.1, chloroform)

d. Preparation of the final compound, 1-N-((S)-4-amino-2-hydroxybutyryl)-3'-deoxy-5-O-β-D-xylofuranosylneamine The compound obtained in the step (c) above (24 mg) was dissolved in 80% aqueous ethanol, to which was added a small amount of hydrazine hydrate and the mixture allowed to cause reaction at 60° C for 2 hours. The reaction mixture was concentrated and the concentrate was treated with chloroform. The chloroform-insoluble matter was taken out and mixed with acetone. The mixture was allowed to stand overnight in an ice box. The acetone-insoluble matter thus separated was chromatographed in a column of CM-Sephadex C-25 by developing with 0.1–0.4N aqueous ammonia. Active fractions containing the desired final compound were combined together and concentrated to dryness, affording the titled compound. Yield 5.1 mg; $[\alpha]_D^{20}$ +22° (c 1, water)

EXAMPLE 6 a. Preparation of 5-O-(2,3,5-tri-O-benzoyl-β-D-xylofuranosyl)-3'-deoxy-4'-O-α-naphthoyl-3,2',6'-tri-N-phenoxycarbonylneamine 1,6-carbamate of the formula:

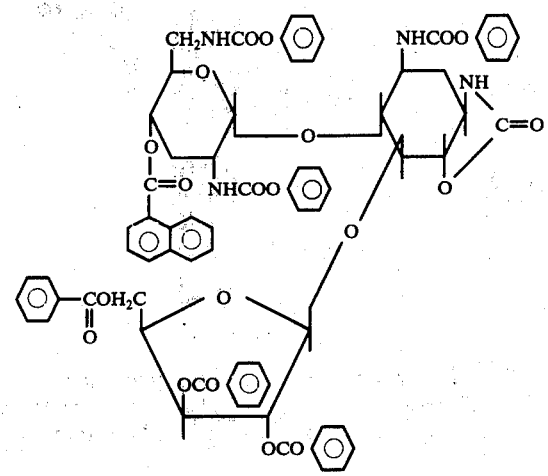

3'-deoxy-4'-O-α-naphthoyl-3,2',6'-tri-N-phenoxycarbonylneamine 1,6-carbamate (80 mg) which was prepared as in Example 18 given later and which has the formula:

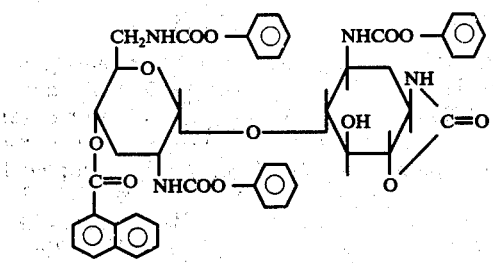

was suspended in anhydrous dichloromethane (1 ml) and condensed with tri-O-benzoyl-D-xylofuranoxyl bromide (70 mg) in the same manner as in Example 4(a). The reaction mixture was after-treated in the same manner as in Example 4(a), affording the titled compound. Yield 76 mg; $[\alpha]_D^{20}$ +17° (c 1, chloroform)

Elementary analysis: Calculated for $C_{71}H_{62}N_4O_{20}$: C 66.04; H 4.84; N 4.34%, Found: C 65.81; H 4.73; N 4.24%.

b. Preparation of the final compound, 1-N-((S)-4-amino-2-hydroxybutyryl)-3'-deoxy-5-O-β-D-xylofuranosylneamine The compound obtained in the step (a) above (70 mg) was treated by the same procedures as described in Example 3(b), (c) and (d), affording the titled compound. Yield 28 mg;

EXAMPLE 7

Preparation of 5-O-(2,3,5-tri-O-benzoyl-β-D-xylofuranosyl)-3,2'-di-N-benzyloxycarbonyl-3'-deoxyneamine 1,6;4',6'-dicarbamate of the formula:

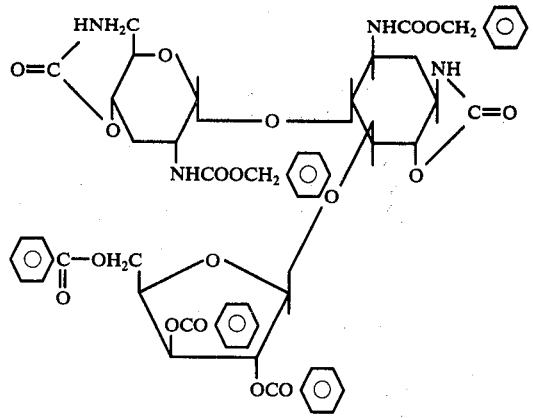

3,2'-di-N-benzyloxycarbonyl-3'-deoxyneamine 1,6;4',6'-dicarbamate (58 mg) which was prepared as in Example 19 given later and which has the formula:

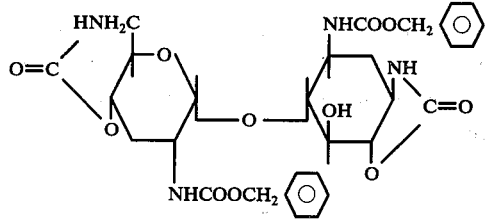

was suspended in anhydrous dichloromethane (1 ml) and condensed with tri-O-benzoyl-D-xylofuranosyl bromide (70 mg) in the same manner as in Example 1(a). The reaction mixture was after-treated in the same manner as in Example 1(a), affording the titled compound.

Yield 17 mg; $[\alpha]_D^{20}$ +16° (c 0.5; chloroform), Elementary analysis: Calculated for $C_{56}H_{54}N_4O_{19}$: C 61.87; H 5.01; N 5.15% Found: C 62.07; H 5.13; N 5.12%.

b. Preparation of 3,2'-di-N-benzyloxycarbonyl-3'-deoxy-5-O-β-D-xylofuranosylneamine 4',6'-carbamate of the formula:

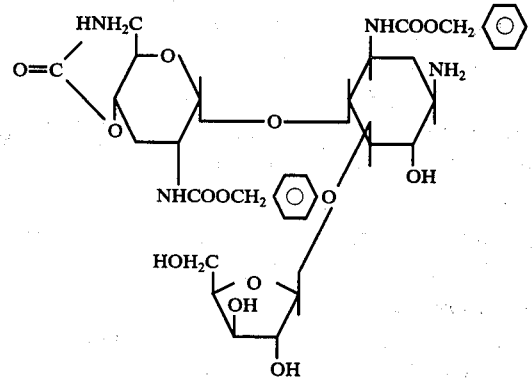

The compound obtained in the step (a) above (15 mg) was dissolved in dioxane (2 ml), to which was then slowly added 0.05N barium hydroxide solution at 50° C. The reaction was stopped at such a point that the reaction mixture has stably become slightly alkaline, and the reaction mixture was neutralized with carbon dioxide gas. Precipitate thus deposited was filtered and the filtrate was concentrated to dryness, leaving a solid matter. The solid was dissolved in aqueous dioxane (water:dioxane 1:5) and the solution was filtered and then distilled to remove the solvent. Yield 11 mg c. Preparation of the final compound, 1-N-((S)-4-amino-2-hydroxybutyryl)-3'-deoxy-5-O-β-D-xylofuranosylneamine The compound obtained in the step (b) above (10 mg) was treated with (S)-2-hydroxy-4-phthaloylaminobutyric acid (10 mg) for condensing the latter with the 1-amino group of the former in the same manner as in Example 5(b). Then, the procedures of Example 5(c) and (d) were followed to give the titled compound. Yield 3.5 mg

EXAMPLE 8 a. Preparation of 6'-azido-3,2'-di-N-benzyloxycarbonyl-3',6'-dideoxy-4'-O-(α-nephthoyl)-5-O-(2,3,5-tri-O-p-nitrobenzoyl-β-D-ribofuranosyl)paromamine 1,6-carbamate of the formula:

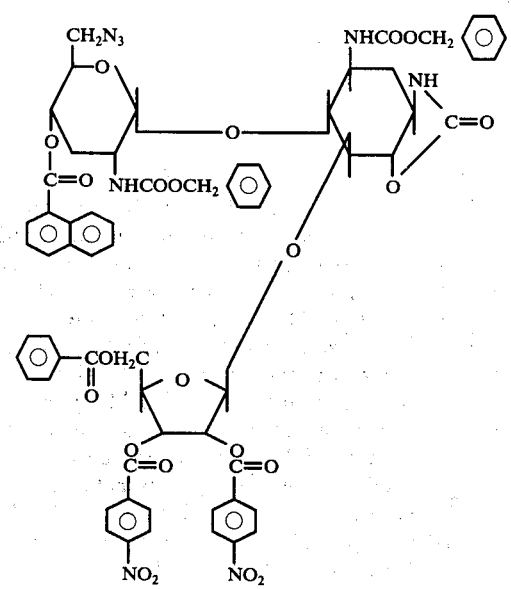

6'-azido-3,2'-di-N-benzyloxycarbonyl-3',6'-dideoxy-4'-O-(α-naphthoyl)paromanine 1,6-carbamate (103 mg) which was prepared as in Example 15 given later and which has the formula:

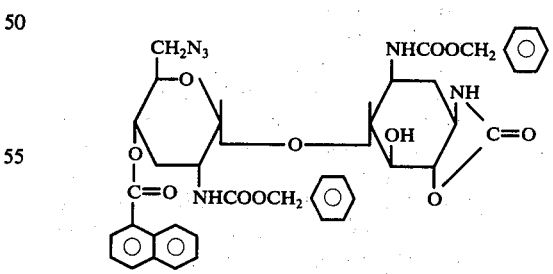

was suspended in anhydrous dichloromethane (2 ml), to which were added anhydrous calcium sulfate (600 mg), mercuric cyanide (350 mg) and then 2,3,5-tri-O-(p-nitrobenzoyl)-D-ribofuranosyl bromide (330 mg), and the mixture was vigorously stirred overnight. Insoluble matters were filtered off and well washed with dichloromethane. The filtrate was combined with the said washing and the mixture was washed with saturated sodium hydrogen carbonate solution and then with water, dried over anhydrous sodium sulphate and distilled to remove the solvent. The residue was purified by chromatography on silica-gel column using chloroform-ethyl acetate (3:1 by weight) as developer. The eluate was collected in 2 ml fractions and fractions containing the desired compound were combined together and concentrated to dryness, affording the titled compound.

Yield 119 mg; $[\alpha]_D^{22}$ +25° (c 1, chloroform) Elementary analysis: Calculated for $C_{66}H_{57}N_9O_{24}$: C 58.28; H 4.22; N 9.27% Found: C 58.04; H 4.32; N.8.99%.

b. Preparation of 6'-azido-3,2'-di-N-benzyloxycarbonyl-3',6'-dideoxy-5-O-β-D-ribofuranosylparomamine The compound obtained in the step (a) above (462 mg) was dissolved in dioxane (20 ml) and treated with 0.1N barium hydroxide solution (20 ml) in the same manner as in Example 1(e), affording the titled compound. Yield 245 mg.

c. Preparation of 1-N-((S)-4-amino-2-hydroxybutyryl)-3'-deoxy-5-O-β-D-ribofuranosylneamine (i.e. 3'-deoxybutirosin B)

According to the procedures of Examples 1(f) and (g), the compound obtained in the step (b) above was converted to the titled compound.

EXAMPLE 9 a. Preparation of 6'-azido-5-O-(2,3,5-tri-O-benzoyl-β-D-xylofuranosyl)-3,2'-N-benzyloxycarbonyl-3',6'-dideoxy-4'-O-α-naphthoylparomamine 1,6-carbamate of the formula:

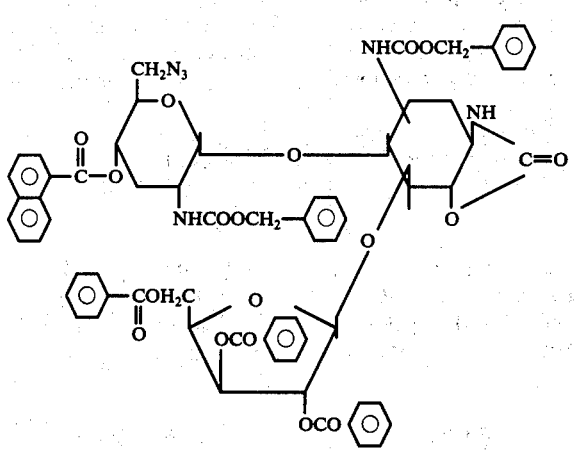

Tetra-O-benzoyl-D-xylofuranose (170 mg) was treated by the method described in literature [J. J. Fox, J. F. Codington, N. C. Yung, L. Kaplan and J. O. Lampen: Journal of the American Chemical Society, 80, 5155 (1958)], yielding the corresponding sugar bromide.

6'-azido-3,2'-di-N-benzyloxycarbonyl-3',6'-dideoxy-4'-O-(α-naphthoyl)paromamine 1,6-carbamate (78 mg) which was prepared as in Example 15 given later was suspended in anhydrous dichloromethane (1 ml), to which were added anhydrous calcium sulfate (400 mg), mercuric cyanide (170 mg) and then the sugar bromide prepared as above (0.3 ml) in the form of a dichloromethane solution, and the mixture was vigorously stirred overnight.

Insoluble matters were filtered off and well washed with dichloromethane. The filtrate was combined with the said washing and the mixture was washed with saturated sodium hydrogen carbonate solution and then with water, dried over anhydrous sodium sulfate and distilled to remove the solvent. The residue was purified by chromatography on silica-gel column using chloroform-ethyl acetate (2:1 by volume) as developer. The eluate was collected in 3 ml fractions and fractions containing the desired compound were combined together and concentrated to dryness, affording the titled compound. Yield 75 mg; $[\alpha]_D^{20}$ +18.5° (c 1, chloroform)

Elementary analysis: Calculated for $C_{66}H_{60}N_6O_{18}$: C 64.70; H 4.94; N 6.86%, Found: C 64.93; H 4.81; N 6.66%.

b. Preparation of 6'-azido-3,2'-di-N-benzyloxycarbonyl-3',6'-dideoxy-5-O-β-D-xylofuranosylparomamine of the formula:

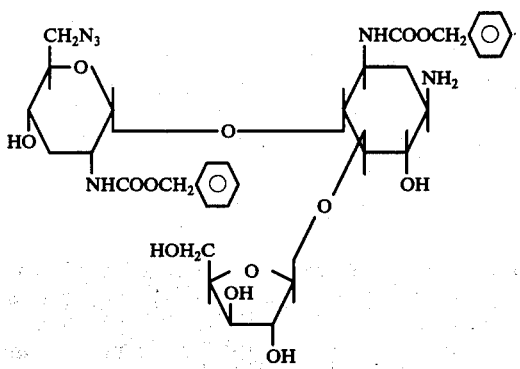

The compound obtained in the step (a) above (60 mg) was dissolved in dioxane (3 ml), to which was slowly added 0.1N barium hydroxide solution (3.3 ml) over 3 hours at 60° C under stirring. Carbon dioxide was blown into the reaction mixture whereby precipitation occurred. The precipitate thus deposited was filtered off and the filtrate was concentrated to dryness. The solid residue was dissolved in dioxane and the solution was filtered. The filtrate was concentrated to dryness, affording the titled compound. Yield 39.8 mg. IR spectrum: 2100; 1700 cm$^{-1}$ c. Preparation of 6'-azido-3,2'-di-N-benzyloxycarbonyl-1-N-((S)-4-benzyloxycarbonylamino-2-hydroxybutyryl)-3',6'-dideoxy-5-O-β-D-xylofuranosylparomamine The compound obtained in the step (b) above (50 mg) was dissolved in tetrahydrofuran (0.8 ml) and subjected to 1-N-acylation and after-treated in the same manner as in Example 1(f), affording the titled compound.

Yield 19 mg, Elementary analysis, Calculated for $C_{45}H_{57}N_7O_{17}$: C 55.84; H 5.94; N 10.13%, Found: C 55.93; H 5.70; N 9.80%.

d. Preparation of the final compound, 1-N-((S)-4-amino-2-hydroxybutyryl)-3'-deoxy-5-O-β-D-xylofuranosylneamine (3'-deoxybutirosin A)

The compound obtained in the step (c) above (35 mg) was dissolved in dioxane (0.6 ml) and the solution was treated in the same manner as in Example 1(g), affording the titled compound. Yield 10 mg; $[\alpha]_D^{20}$ +23° (c 1, water).

EXAMPLE 10 a. Preparation of 6'-azido-3,2'-N-benzyloxycarbonyl-1-N-(RS)-3-benzyloxycarbonylamino-2-hydroxy-propionyl)-3',6'-dideoxy-5-O-β-D-xylofuranosylparomamine of the formula:

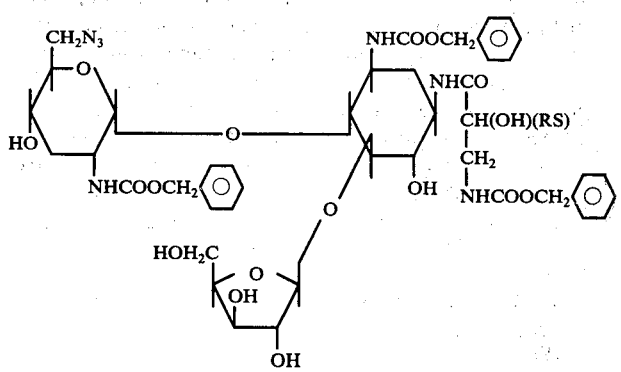

6'-azido-3,2'-di-N-benzyloxycarbonyl-3',6'-dideoxy-5-O-β-D-xylofuranosylparomamine (50 mg) prepared as in Example 9(b) was dissolved in tetrahydrofuran (0.8 ml), to which were then added N-hydroxysuccinimide ester of (RS)-3-benzyloxycarbonylamino-2-hydroxypropionic acid (30 mg) and triethylamine (10 mg), and the mixture was allowed to stand for reaction at room temperature for one hour. The reaction mixture was after-treated in the same manner as in Example 1(f), affording the titled compound as solid. Yield 26 mg; $[\alpha]_D^{22}$ +15° (c 0.2, chloroform).

b. Preparation of the final compound, 1-N-((RS)-3-amino-2-hydroxypropionyl)-3'-deoxy-5-O-α-D-xylofuranosylneamine The compound obtained in the step (a) above (32 mg) was dissolved in dioxane (0.6 ml) and the solution was treated in the same manner as in Example 1(g), affording the titled compound. Yield 9.6 mg; $[\alpha]_D^{20}$ +25.5° (c 1, water).

EXAMPLE 11 a. Preparation of 6'-azido-3,2'-di-N-benzyloxycarbonyl-1-N-((S)-3-benzyloxycarbonylamino-2-hydroxypropionyl)-3',6'-dideoxy-5-O-α-D-xylofuranoxylparomamine 6'-azido-3,2'-di-N-benzyloxycarbonyl-3',6'-dideoxy-5-O-β-D-xylofuranosylparomamine (50 mg) prepared as in Example 9(b) was dissolved in tetrahydrofuran (0.8 ml), to which were added N-hydroxysuccinimide ester of (S)-3-benzyloxycarbonylamino-2-hydroxypropionic acid (30 mg) and triethylamine, and the mixture was allowed to stand for reaction at room temperature for one hour. The reaction mixture was then after-treated in the same manner as in Example 1(f), affording the titled compound as solid. Yield 25 mg; $[\alpha]_D^{20}$ +13° (c 0.2; chloroform)

Elementary analysis:

Calculated for $C_{44}H_{55}N_7O_{17}$: C 55.40; H 5.81; N 10.28%, Found: C 55.36; H 5.72; N 10.38%.

b. Preparation of the final compound, 1-N-((S)-3-amino-2-hydroxypropionyl)-3'-deoxy-5-O-α-D-xylofuranosylneamine of the formula:

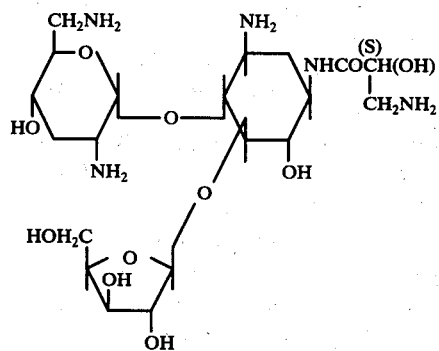

The compound obtained in the step (a) above (32 mg) was dissolved in dioxane (0.6 ml) and the solution was treated in the same manner as in Example 1(g), affording the titled compound as solid. Yield 9.8 mg; $[\alpha]_D^{20}$ +21°(c 1, water)

Elementary analysis:

Calculated for $C_{20}H_{39}N_5O_{11}\cdot H_2CO_3$: C 42.92; H 7.03; N 11.92%, Found: C 43.08; H 6.93; N 11.71%.

EXAMPLE 12 a. Preparation of 5-O-(2,3,5-tri-O-acetyl-α-L-arabinofuranosyl)-6'-azido-3,2'-di-N-benzyloxycarbonyl-3',6'-dideoxy-4'-O-α-naphthoylparomamine 1,6-carbamate of the formula:

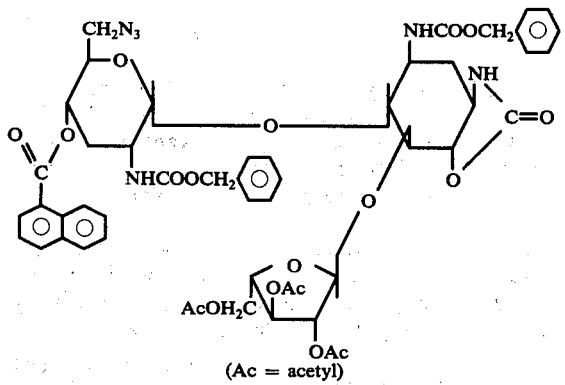

(Ac = acetyl)

Methyl tri-O-benzoyl-α-L-arabinofuranoside (502 mg) which was prepared by a known method [R. Barker and H. G. Flecher, Jr.: Journal of Organic Chemistry, 26, 4605 (1961)] was treated with sodium methoxide in methanol (5 ml) to yield methyl α-L-arabinofuranoside. The compound obtained (130 mg)

was treated with acetic anhydride (0.3 ml) in pyridine (3 ml) to give methyl tri-O-acetyl-α-L-arabinofuranoside. The compound obtained (108 mg) was dissolved in acetic acid (1 ml), to which were added acetic anhydride (0.05 ml) and acetic acid saturated with hydrogen bromide (0.25 ml) and the mixture was allowed to stand at 60° C for 2 hours. The reaction mixture was then concentrated under a reduced pressure to yield a syrup of the corresponding sugar bromide.

The syrup was dissolved in anhydrous dichloromethane, to which were added anhydrous calcium sulfate (170 mg), 6'-azido-3,2'-di-N-benzyloxycarbonyl-3',6'-dideoxy-4'-O-(α-naphthoyl)paromamine 1,6-carbamate (104 mg) and then mercuric cyanide (173 mg), and the mixture was vigorously stirred at room temperature overnight. The reaction mixture was filtered and the filtrate was washed with aqueous sodium hydrogen carbonate solution and then with water, dried over anhydrous sodium sulfate and concentrated to give a solid containing the desired compound. The solid was purified by silica-gel column chromatography using chloroform-ethanol (50:1 by volume) as developer. The eluate was collected in 5 ml fractions and fractions containing the desired compound were combined together and concentrated to dryness, affording the titled compound. Yield 98 mg; $[\alpha]_D^{20}$ +26° (c 1, chloroform)

Elementary analysis: Calculated for $C_{51}H_{54}N_6O_{18}$: C 58.95; H 5.24; N 8.09%, Found: C 58.87; H 5.31; N 7.82%.

b. Preparation of 5-O-α-L-arabinofuranosyl-6'-azido-3,2'-di-N-benzyloxycarbonyl-3',6'-dideoxyparomamine The compound obtained in the step (a) above (60 mg) was dissolved in dioxane (30 ml) and the solution was treated in the same manner as in Example 1(e), affording the titled compound. Yield 37 mg.

c. Preparation of 5-O-α-L-arabinofuranosyl-6'-azido-3,2'-di-N-benzyloxycarbonyl-1-N-((S)-4-benzyloxycarbonylamino-2-hydroxybutyryl)-3',6'-dideoxyparomamine The compound obtained in the step (b) above (50 mg) was dissolved in tetrahydrofuran (0.8 ml) and the solution was reacted with N-hydroxysuccinimide ester of (S)-4-benzyloxycarbonylamino-2-hydroxybutyric acid (30 mg) and after-treated in the same manner as in Example 1(f), yielding the titled compound. Yield 17 mg; $[\alpha]_D^{20}$ +20° (c 1, chloroform)

Elementary analysis: Calculated for $C_{45}H_{57}N_7O_{17}$: C 55.84; H 5.94; N 10.13%, Found: C 55.71; H 5.75; N 10.06%.

d. Preparation of the final compound, 1-N-((S)-4-amino-2-hydroxybutyryl)-5-O-α-L-arabinofuranosyl-3'-deoxyneamine of the formula:

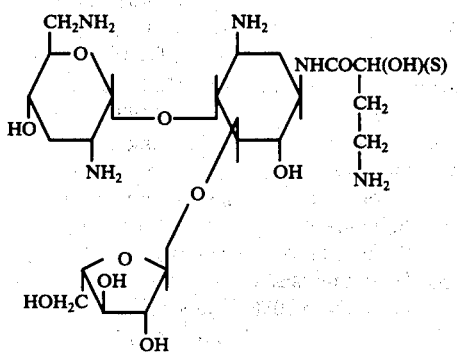

The compound obtained in the step (c) above (35 mg) was dissolved in dioxane (0.6 ml) and the solution was treated in the same manner as in Example 1(g), affording the titled compound. Yield 88 mg; $[\alpha]_D^{20}$ +29° (c 1, water)

Elementary analysis: Calculated for $C_{21}H_{41}N_5O_{11}\cdot H_2CO_3$: C 43.92; H 7.20; N 11.64%, Found: C 44.30; H 7.11; N 11.33%.

EXAMPLE 13 a. Preparation of tri-N-benzyloxycarbonyl-3'-deoxyparomamine

3'-deoxyparomamine (5.32 g) was dissolved in water (26 ml), to which were added sodium carbonate (5.4 g) and then methanol (85 ml) under stirring. To the resulting mixture which contained precipitate was added benzyl chloroformate ($ClCOOCH_2C_6H_5$) (7.08 g) drop by drop under stirring. After the lapse of 2 hours, the reaction mixture was filtered and the filter cake was washed with water and ethyl ether and dried to yield the titled compound. Yield 9.0 g; $[\alpha]_D^{22}$ +43° (c 0.5; dioxane)

Elementary analysis: Calculated for $C_{36}H_{43}N_3O_{12}$: C 60.92; H 6.11; N 5.92%, Found: C 60.70; H 6.06; N 5.63%. b. Preparation of 3,2'-di-N-benzyloxycarbonyl-3'-deoxyparomamine 1,6-carbamate of the formula:

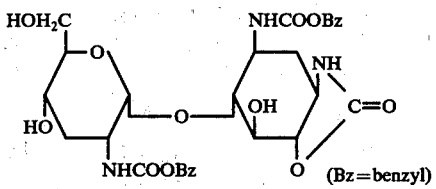

The compound obtained in the step (a) above (10 g) was dissolved in anhydrous dimethylformamide (250 ml), to which was added 50% oily sodium hydride (2 g) and the mixture was stirred for 2.5 hours under ice-cooling. After the addition of acetic acid (4 ml), the reaction mixture was concentrated and the concentrate was poured into ice water. The precipitate thus deposited was filtered off, washed with water and dried, affording the titled compound. Yield 6.6 g.

c. Preparation of 4',6'-O-benzylidene-3,2'-di-N-benzyloxycarbonyl-3'-deoxyparomamine 1,6-carbamate The compound obtained in the step (b) above (1.2 g) was dissolved in anhydrous dimethylformamide (25 ml), to which were added p-toluenesulfonic acid (70 mg) and benzaldehyde dimethylacetal (3 g), and the mixture was heated at 50° C under 30 mm Hg for 1 hour. The solution was substantially concentrated under a reduced pressure and the concentrate was dissolved in a large amount of chloroform. The chloroform solution was washed with sodium hydrogen carbonate solution and then with water, dried over anhydrous sodium sulfate and concentrated to dryness affording the titled compound.

Yield 1.16 g; $[\alpha]_D^{20}$ +32° (c 1, dioxane); IR spectrum: 1760 $cm^{-1}$ (cyclic carbamate); Elementary analysis: Calculated for $C_{36}H_{39}N_3O_{11}$: C 62.69; H 5.70; N 6.09%, Found: C 62.47; H 5.68; N 6.12%.

EXAMPLE 14 a. Preparation of tri-N-benzyloxycarbonyl-4',6'-O-cyclohexylidene-3'-deoxyparomamine of the formula:

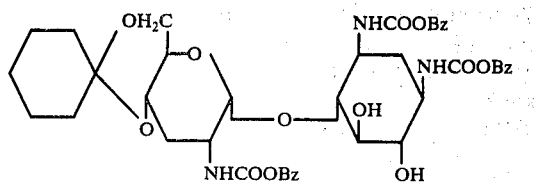

Tri-N-benzyloxycarbonyl-3'-deoxyparomamine (2.5 g) was dissolved in dimethylformamide (40 ml), to which were added p-toluenesulfonic acid (100 mg) and 1,1-dimethoxycyclohexane (4 ml), and the mixture was heated at 50° C for 1 hour. The reaction solution was substantially concentrated under a reduced pressure, and to the concentrate was added 60% aqueous acetic acid (50 ml) and the mixture was warmed at 30° C for further 1 hour. Then, sodium hydrogen carbonate (200 mg) was added to the mixture and the latter was concentrated to dryness. The residue was dissolved in chloroform and the solution was washed with water, dried over anhydrous sodium sulfate and concentrated under a reduced pressure to dryness, yielding the titled compound. Yield 2.7 g; $[\alpha]_D^{18}$ +31° (c 1, chloroform)

b. Preparation of 3,2'-di-N-benzyloxycarbonyl-4',6'-O-cyclohexylidene-3'-deoxyparomamine 1,6-carbamate The compound obtained in the step (a) above (1.52 g) was dissolved in anhydrous dimethylformamide (25 ml), to which was added 50% oily sodium hydride (250 mg) and the mixture was stirred for 3 hours under ice-cooling. The reaction mixture was after-treated in the same manner as in Example 1(b), affording the titled compound.

Yield 1.09; $[\alpha]_D^{20}$ +52° (c 1, pyridine), Elementary analysis: Calculated for $C_{35}H_{43}N_3O_{11}$: C 61.66; H 6.36; N 6.16%, Found: C 61.38; H 6.41; N 6.08%.

EXAMPLE 15 a. Preparation of tri-N-benzyloxycarbonyl-3'-deoxy-6'-O-tosylparomamine

Tri-N-benzyloxycarbonyl-3'-deoxyparomamine (9.78 g) was dissolved in anhydrous pyridine (200 ml), to which was added p-toluenesulfonyl chloride (3.5 g) and the mixture was allowed to stand at −10° C overnight. After the addition of a small amount of water, the reaction solution was concentrated. The resulting syrup was dissolved in chloroform and the solution was washed with water, dried over anhydrous sodium sulfate and concentrated to dryness, yielding the titled compound.

Yield 8.08 g; mp. 185°-186° C; $[\alpha]_D^{21}$ +33° (c 1, dioxane) Elementary analysis: Calculated for $C_{43}H_{49}N_3O_{14}S$: C 59.78; H 5.72; N 4.86; S 3.71%, Found: C 59.89; H 5.70; N 4.87; S 3.72%.

b. Preparation of tri-N-benzyloxycarbonyl-3'-deoxy-6'-O-mesylparomamine

Tri-N-benzyloxycarbonyl-3'-deoxyparomamine was treated with mesyl chloride in a similar manner as in Example 15(a), affording the titled compound. Yield 62%; $[\alpha]_D^{20}$ +35° (c 1, dioxane)

c. Preparation of 6'-azido-tri-N-benzyloxycarbonyl-3',6'-dideoxyparomamine

The compound obtained in the step (a) above (5.46 g) was dissolved in dimethylformamide (100 ml), to which was added sodium azide (4.2 g) and the mixture was stirred at 60° C for 7 hours. The resulting solution was filtered and the filtrate was concentrated. Then, an amount of toluene was added to the concentrate and the concentration operation was repeated to remove the dimethylformamide. The residue was dissolved in dioxane and the solution was filtered and concentrated to dryness, affording the titled compound. Yield 4.23 g; mp. 206°-209° C; $[\alpha]_D^{22}$ +90° (c 0.5, dioxane);

IR spectrum 2100 cm$^{-1}$ ($N_3$ group), Elementary analysis: Calculated for $C_{36}H_{42}N_6O_{11}$: C 58.85; H 5.76; N 11.44%, Found: C 58.87; H 5.78; N 11.20%.

d. The same compound as that prepared by the step (c) above was obtained by treating the compound obtained in the step (b) above in the same manner as in the step (c) above. Yield 93% e. Preparation of 6'-azido-3,2'-di-N-benzyloxycarbonyl-3',6'-dideoxyparomamine 1,6-carbamate The compound obtained in the step (c) above (1.1 g) was dissolved in anhydrous dimethylformamide (22 ml), to which was added 50% oily sodium hydride (240 mg) and the mixture was stirred for 2.5 hours under ice-cooling. After the addition of acetic acid (0.35 ml), the reaction mixture was poured into ice-water. The precipitate thus deposited was filtered off and washed with water and dried. The resulting solid was dissolved in dioxane, to which was then added n-hexane, whereby the titled compound was deposited as precipitate and recovered.

Yield 0.75 g; $[\alpha]_D^{20}$ +73° (c 1, dioxane); IR spectrum 2100 ($N_3$), 1750 (cyclic carbamate), 1700 (urethane carbonyl), 1520 (amide II), Elementary analysis: Calculated for $C_{29}H_{34}N_6O_{10}$: C 55.59; H 5.47; N 13.41% Found: C 55.67; H 5.50; N 12.91%.

f. Preparation of 6'-azido-3,2'-di-N-benzyloxy-carbonyl-3',6'-dideoxy-4'-O-(α-naphthoyl)paromamine 1,6-carbamate The compound obtained in the step (e) above (1.03 g) was dissolved in anhydrous pyridine (20 ml) and the solution was cooled by ice-common salt. α-naphthoyl chloride (370 mg) was added to the cooled solution and the mixture was allowed to stand overnight at −10° C. After the addition of water (0.05 ml), the reaction solution was concentrated to a syrup. The syrup was dissolved in chloroform and the solution was washed with water, dried and concentrated to dryness. The solid residue was purified by chromatography on silica-gel column using benzene-ethyl acetate (1:1 by volume) as developer, yielding the titled compound. Yield 826 mg; $[\alpha]_D^{23}$ +98° (c 1, dioxane) Elementary analysis: Calculated for $C_{40}H_{40}N_6O_{11}$: C 61.53; H 5.17; N 10.76% Found: C 61.42; H 5.24; N 10.49%,

EXAMPLE 16

Preparation of 3,2',6'-tri-N-benzyloxycarbonyl-3'-deoxy-4'-O-α-naphthoylneamine 1,6-carbamate.

The compound obtained in Example 15(f) (320 mg) was dissolved in water-dioxane (1:9 by volume; 10 ml) and the solution was subjected to reduction with palladium-hydrogen system in a conventional manner. The resulting solution was filtered, and to the filtrate were added a small amount of sodium hydrogen carbonate and benzyl chloroformate ($ClCOOCH_2C_6H_5$) (285 mg) and the mixture was stirred at room temperature for 1 hour. The reaction solution was concentrated to dryness and the residue was extracted with chloroform. The chloroform solution was washed with water, dried over anhydrous sodium sulfate and distilled to remove the solvent, yielding the titled compound. Yield 281 mg; $[\alpha]_D^{20}$ +83° (c 1, chloroform)

Elementary analysis: Calculated for $C_{48}H_{48}N_4O_{13}$: C 64.85; H 5.44; N 6.30% Found: C 65.13; H 5.32; N 6.08%.

EXAMPLE 17

Preparation of 3'-deoxy-3,2',6'-tri-N-ethoxycarbonyl-4'-O-α-naphthoylneamine 1,6-carbamate.

The procedure of Example 16 was repeated except that ethyl chloroformate ($ClCOOC_2H_5$) was used in place of benzyl chloroformate. There was obtained the titled compound.

Yield 73%; $[\alpha]_D^{18}$ +90° ( C 1, chloroform), Elementary analysis: Calculated for $C_{33}H_{42}N_4O_{13}$: C 56.30; H 5.88; N 7.76%, Found: C 56.40, H 6.02; N 7.97%,

EXAMPLE 18

Preparation of 3'-deoxy-4'-O-α-naphthoyl-3,2',6'-tri-n-phenoxycarbonylneamine 1,6-carbamate, The procedure of Example 16 was repeated except that phenyl chloroformate ($ClCOOC_6H_5$) was used in place of benzyl chloroformate. The titled compound was obtained.

Yield 64%; $[\alpha]_D^{18}$ +83° (c 0.5, chloroform) Elementary analysis: Calculated for $C_{45}H_{42}N_4O_{13}$: C 63.82; H 5.00; N 6.62%, Found: C 63.96; H 4.81; N 6.43%.

EXAMPLE 19

Preparation of 3,2'-di-N-benzyloxycarbonyl-3'-deoxyneamine 1,6;4',6'-dicarbamate 3'-deoxyneamine (6.2 g) was reacted with benzyl chloroformate (8.0 g) in a similar manner as in Example 13(a) to ogtain tetra-N-benzyloxycarbonyl-3'-deoxyneamine (9.5 g). The latter (2.3 g) was dissolved in dimethylformamide (40 ml), to which was then added 50% oily sodium hydride (300 mg) and the mixture was stirred for 2.5 hours under ice-cooling. After the addition of acetic acid (0.05 ml), the reaction mixture was concentrated and the concentrate was poured into ice-water. The precipitate thus deposited as filtered off, washed with water and dried, yielding the titled compound. Yield 1.21 g; $[\alpha]_D^{21}$ +90°0 (c 1, dimethylformamide).

Elementary analysis:
Calculated for $C_{30}H_{24}N_4O_{11}$: C 57.50; H 5.47; N 8.94%, Found: C 57.63; H 5.55; N 8.74%.

EXAMPLE 20

Preparation of 2,3,5-tri-O-(p-nitrobenzoyl)-D-ribofuranosyl bromide.

D-ribose (2.0 g) was dissolved in methanol (40 ml), to which was added 1N methanolic HCl solution (4 ml) and the mixture was allowed to stand at 5° C to produce methyl β-D-ribofuranoside. The compound formed was dissolved in pyridine (50 ml) and the solution was subjected to action of nitrobenzoyl chloride 8.2 g at room temperature. The solvent was distilled off and the residue was dissolved in chloroform. The solution was washed with saturated sodium hydrogen carbonate solution, dried over anhydrous sodium sulfate and distilled to remove the solvent therefrom. Methyl 2,3,5-tri-O-(p-nitrobenzoyl)-β-D-ribofuranoside (4.2 g) thus obtained was dissolved in anhydrous dichloromethane (20 ml). To the solution was added acetic acid (20 ml) which had been saturated with hydrogen bromide under ice-cooling and the mixture was allowed to stand in the dark for 1 hour. The reaction solution was concentrated under a reduced pressure and the resulting sprupy concentrate was dissolved in dichloromethane. The solution was washed with a sodium hydrogen carbonate solution, dried over anhydrous sodium sulfate and distilled to remove the solvent therefrom. The residue was recrystallized from anhydrous benzene to obtain the titled compound. Yield 3.4 g.

Elementary analysis: Calculated for $C_{26}H_{18}N_3O_{13}Br$: C 47.29; H 2.75; N 6.36; Br 12.10%, Found: C 47.07; H 2.44; N 6.17; Br 12.43%.

EXAMPLE 21

Preparation of 2,3-di-O-acetyl-5-O-(p-toluene-sulfonyl)-D-xylofuranosyl bromide.

1,2-O-isopropylidene-5-O-(p-toluenesulfonyl)-α-D-xylofuranose (3.44 g) which was prepared by the known method reported by R. A. Levene and A. L. Raymand in Journal of Biological Chemistry, 102, 317 (1933) was dissolved in acetic acid (53 ml). To the solution were added acetic anhydride (6 ml) and then, under ice-cooling, concentrated sulfuric acid (3.2 ml) with a precaution for keeping the temperature not higher than 15°0 C. The resulting mixture was allowed to stand at room temperature overnight and poured into ice-water and the aqueous mixture was extracted with chloroform (50 ml × 3). The chloroform extracts were combined together, washed with a sodium hydrogen sulfate solution and then with water, dried over anhydrous sodium sulfate and distilled to remove the solvent therefrom. 1,2,3-tri-O-acetyl-5-O-(p-toluenesulfonyl)-D-xylofuranose (4.2 g) thus obtained was dissolved in dichloromethane (75 ml) and the solution was maintained at 0° C and saturated with hydrogen bromide gas. The mixture was allowed to stand at 0° C for 3 hours, concentrated to dryness, affording the titled compound in the form of a syrup. Yield 4.95 g.

What we claim is:

1. A compound of the formula (I'):

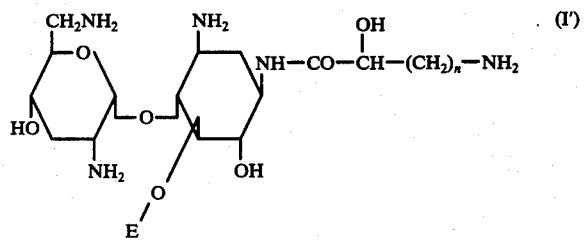

wherein E is β-D-xylofuranosyl group, α-L-arabinofuranosyl group or 5-amino-5-deoxy-β-D-xylofuranosyl group, and n is an integer of 1 or 2, provided that E is β-D-xylofuranosyl group when n is 1 and provided that E is α-L-arabinofuranosyl or 5amino-5-deoxy-β-D-xylofuranosyl group when n is 2, or a pharmaceutically acceptable acid-addition salt thereof.

2. A compound which is 1-N-((RS)-3-amino-2-hydroxypropionyl)-3'-deoxy-5-P-β-xylofuranosylneamine;

1-n-((S)-3-amino-2-hydroxypropyonyl)-3'-deoxy-5-O-β-D-xylofuranosylneamine;

1-N-((S)-4-amino-2-hydroxybutyryl)-3'-deoxy-5-0-α-L-arabinofuranosylneamine; or

1-N-((S)-4-amino-2-hydroxybutyryl)-5-O-(5-amino-5-deoxy-β-D-xylofuranosyl)-3'-deoxyneamine.

* * * * *